US008888980B2

(12) United States Patent
Shiraki et al.

(10) Patent No.: US 8,888,980 B2
(45) Date of Patent: Nov. 18, 2014

(54) ELECTROPHORESIS APPARATUS AND CONTROL METHOD THEREOF

(75) Inventors: Yasunori Shiraki, Kyoto (JP); Genki Adachi, Kyoto (JP); Rina Matsumi, Kyoto (JP); Toru Odagaki, Kyoto (JP); Yusuke Nakayama, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 384 days.

(21) Appl. No.: 13/206,263

(22) Filed: Aug. 9, 2011

(65) Prior Publication Data

US 2012/0037508 A1 Feb. 16, 2012

(30) Foreign Application Priority Data

Aug. 10, 2010 (JP) ................................. 2010-179741
Aug. 24, 2010 (JP) ................................. 2010-187503

(51) Int. Cl.
*G01N 27/453* (2006.01)
*G01N 27/447* (2006.01)

(52) U.S. Cl.
CPC .............................. *G01N 27/44713* (2013.01)
USPC ........................... 204/601; 204/451; 204/602

(58) Field of Classification Search
CPC .......... G01N 27/447; G01N 27/44782; G01N 27/44721; G01N 27/44743; G01N 27/44756; G01N 27/44791; B01L 3/5027; B01L 3/502715
See application file for complete search history.

(56) References Cited

U.S. PATENT DOCUMENTS

| 5,021,646 A | 6/1991 | Weinberger et al. | |
| 2002/0079224 A1* | 6/2002 | Chen et al. | 204/603 |
| 2004/0018638 A1* | 1/2004 | Shoji et al. | 436/516 |
| 2006/0006066 A1 | 1/2006 | Yamazaki et al. | |
| 2008/0074646 A1* | 3/2008 | Archibald | 356/51 |
| 2010/0181199 A1 | 7/2010 | Sugiyama et al. | |

FOREIGN PATENT DOCUMENTS

| EP | 1367388 A1 | 12/2003 | |
| JP | S58-021554 A | 2/1983 | |
| JP | 10-246721 | 9/1998 | ........... G01N 27/447 |
| JP | 2003-159054 A | 6/2003 | |
| JP | 2007-107915 | 4/2007 | ........... G01N 27/447 |
| WO | 96/10743 A1 | 4/1996 | |
| WO | 00/23796 A1 | 4/2000 | |
| WO | 2009/127911 A1 | 10/2009 | |

OTHER PUBLICATIONS

Extended European Search Report issued in corresponding European Patent Application No. 11177162.2 dated Jun. 18, 2013.
Office Action issued in counterpart European Patent Application No. 11177162.2 dated Jul. 2, 2014.

\* cited by examiner

*Primary Examiner* — Luan Van
*Assistant Examiner* — Gurpreet Kaur
(74) *Attorney, Agent, or Firm* — Morgan, Lewis & Bockius LLP

(57) ABSTRACT

An electrophoresis apparatus that applies voltage from electrodes that are provided in a capillary flow channel and causes component separation by performing electrophoresis on a specimen that is injected into the capillary flow channel comprises: a physical quantity acquisition unit and a physical quantity determination unit. The physical quantity acquisition unit, with migration solution and specimen injected inside the capillary flow channel, acquires an electrical quantity that occurs in the capillary flow channel at a specified time when voltage is being applied to the electrodes. The physical quantity determination unit determines whether or not the electrical quantity that the physical acquisition unit acquires is within a specified range.

17 Claims, 18 Drawing Sheets

FIG.8

| NUMBER OF TIMES S302 IS PERFORMED | ELECTRIC CURRENT VALUE |
|---|---|
| INITIAL VALUE (S206) | $I_1$ |
| FIRST TIME | $I_{11}$ |
| SECOND TIME | $I_{12}$ |
| FOURTH TIME | $I_{14}$ |
| FIFTH TIME | $I_{15}$ |
| SIXTH TIME | $I_{16}$ |
| ⋮ | ⋮ |

ELECTROPHORESIS APPARATUS AND CONTROL METHOD THEREOF

CROSS-REFERENCE TO RELATED APPLICATION

This application is based upon Japanese Patent Application No. 2010-179741 filed on Aug. 10, 2010, and Japanese Patent Application No. 2010-187503 filed on Aug. 24, 2010. The entire disclosure of Japanese Patent Application No. 2010-179741 and Japanese Patent Application No. 2010-187503 are incorporated in this specification.

FIELD

This application relates generally to an electrophoresis apparatus that causes component separation by a capillary electrophoresis method, and to a control method for that electrophoresis apparatus.

BACKGROUND

Conventionally, a capillary electrophoresis apparatus has been used as an apparatus to analyze the density and amount of certain components contained in a specimen. In this capillary electrophoresis apparatus, after a migration solution has been filled into a capillary flow channel, a specimen is inserted at one end of the capillary flow channel. Next, by applying a voltage to electrodes that are provided at both ends of the capillary flow channel, electric current flows between the electrodes, and a certain component contained in the specimen moves to the other end of the capillary flow channel by the respective electrophoretic mobility. Due to this movement, the certain component of the specimen is separated from the other components, and by detecting the component using an optical method for example, the density and amount of the certain component can be analyzed.

Examples of capillary electrophoresis apparatuses are disclosed in Unexamined Japanese Patent Application KOKAI Publication No. 2007-107915 and Unexamined Japanese Patent Application KOKAI Publication No. H10-246721. In these electrophoresis apparatuses, whether or not migration solution has been filled in the capillary flow channel is constantly determined, so that after filling with migration solution, and before inserting the specimen, a voltage is applied to the electrodes on both ends of the capillary flow channel, and the value of the current flowing between the electrodes is measured.

SUMMARY

By inserting the specimen into the capillary flow channel, the fluid inside the capillary flow channel becomes a mixed state of the migration solution and specimen. In other words, the character of the fluid inside the capillary flow channel changes from before and after the specimen is inserted. Therefore, under conditions of applying the same voltage from the electrodes, the current flowing between the electrodes differs. Consequently, when performing electrophoresis after the specimen has been inserted, it is necessary to set the value of the applied voltage separately from before the specimen was inserted.

Moreover, due to the work of inserting the specimen into the capillary flow channel, air bubbles occur in the fluid inside the capillary flow channel, and foreign matter becomes mixed therein. Therefore, even though the value of the current flowing between electrodes before the specimen is inserted is measured as in the inventions of Unexamined Japanese Patent Application KOKAI Publication No. 2007-107915 and Unexamined Japanese Patent Application KOKAI Publication No. H10-246721, when voltage is applied to the electrodes after the specimen has been inserted in order to perform electrophoretic separation, the current that is expected from the value of the voltage does not flow between the electrodes.

Furthermore, after the specimen has been inserted inside the capillary flow channel, the temperature of the component members of the capillary flow channel changes due to the Joule heat that occurs when voltage is applied. Due to this as well, there is a possibility that the expected current will not flow between the electrodes. There is a high possibility that this problem will occur when voltage is repeatedly applied in order to analyze a plurality of specimens. Moreover, there is also a possibility that, due to changes in the temperature of the environment where the components of the capillary flow channel are located, the expected electric current will not flow between the electrodes.

Taking the above situation into consideration, the object of the present invention is to provide an electrophoresis apparatus that is capable of detecting abnormalities in the capillary flow channel during separation of components during electrophoresis, and a control method for that electrophoresis apparatus.

The electrophoresis apparatus of a first aspect of the present invention is an electrophoresis apparatus that applies voltage from electrodes that are provided in a capillary flow channel and causes component separation by performing electrophoresis on a specimen that is injected into the capillary flow channel, and is characterized by comprising:

a physical quantity acquisition unit that, with migration solution and specimen injected inside the capillary flow channel, acquires an electrical quantity that occurs in the capillary flow channel at a specified time when voltage is being applied to the electrodes; and a physical quantity determination unit that determines whether or not the electrical quantity is within a specified range.

A control method for an electrophoresis apparatus of a second aspect of the present invention is a control method for an electrophoresis apparatus that applies voltage from electrodes that are provided in a capillary flow channel in order to separate components of a specimen injected inside the capillary flow channel by electrophoresis is characterized by comprising:

a physical quantity acquisition step that, with migration solution and specimen injected inside the capillary flow channel, acquires an electrical quantity that occurs in the capillary flow channel at a specified time when voltage is being applied to the electrodes; and a physical quantity determination step of determining whether or not the electrical quantity is within a specified range.

BRIEF DESCRIPTION OF THE DRAWINGS

A more complete understanding of this application can be obtained when the following detailed description is considered in conjunction with the following drawings, in which:

FIG. 8 is a diagram illustrating a table wherein electric current values that are obtained in the determination process during voltage application are recorded;

DETAILED DESCRIPTION (Embodiment 1)

Figure 1:
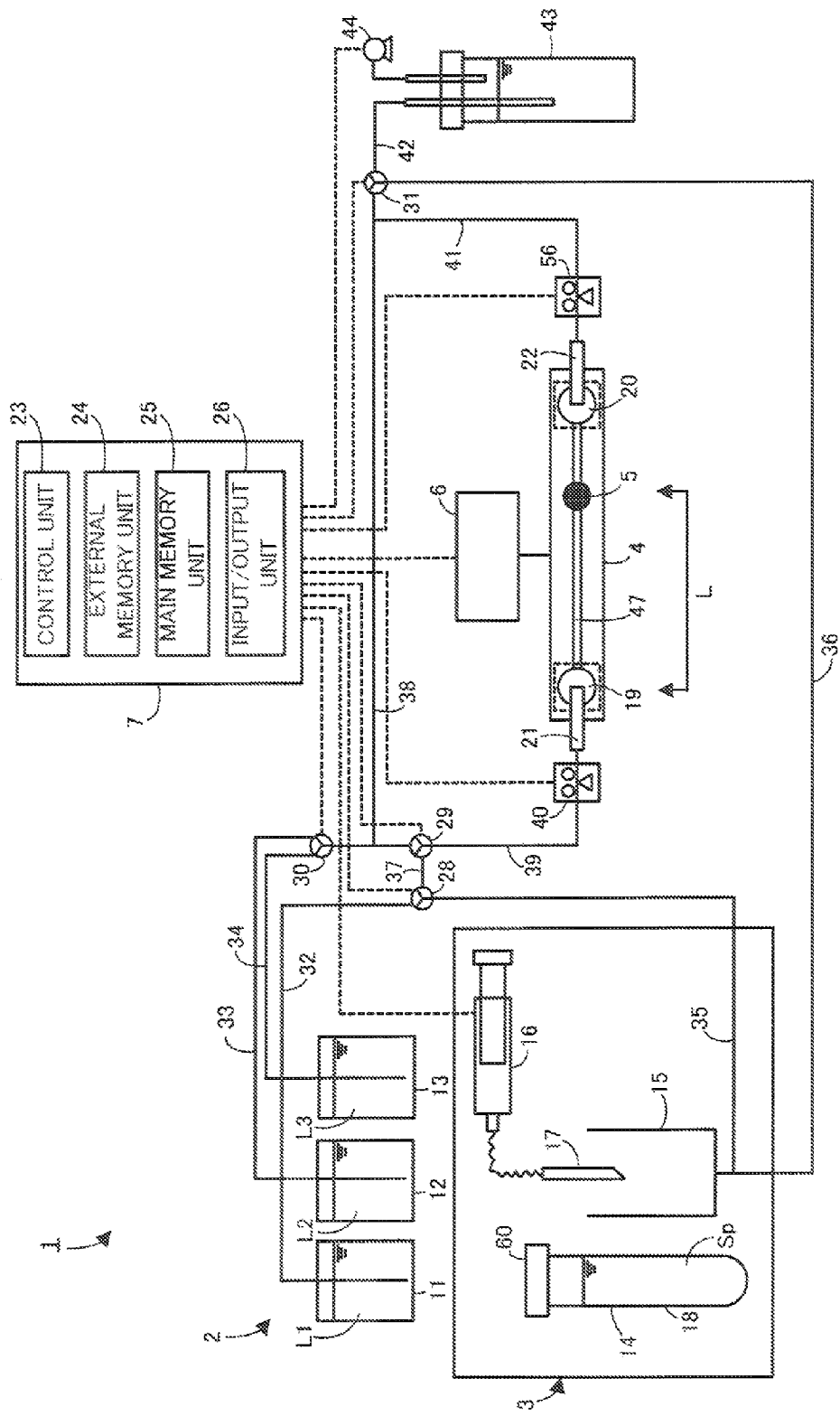
FIG. 1 is a diagram illustrating the construction of an electrophoresis apparatus according to a first embodiment of the present invention.
Figure 2:
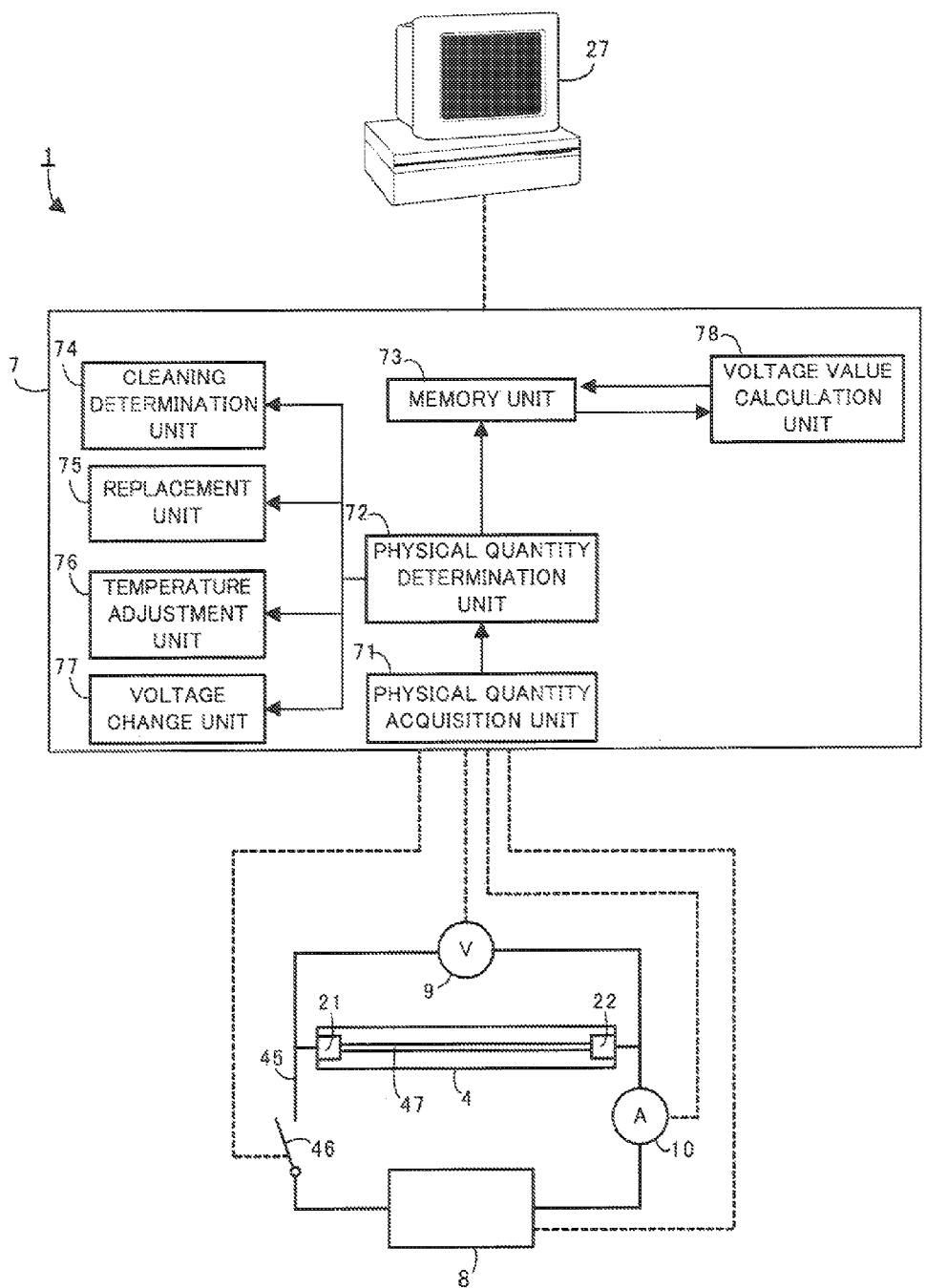
FIG. 2 is a circuit diagram illustrating the construction of the electric power supply of the electrophoresis apparatus of the first embodiment.

FIG. 1 is a diagram illustrating the construction of an electrophoresis apparatus of a first embodiment of the present invention. FIG. 2 is a circuit diagram illustrating the construction of the electric power supply of the electrophoresis apparatus of the first embodiment.

The electrophoresis apparatus 1 comprises a storage tank 2, a dispensing unit 3, a detection unit 5, a temperature adjustment unit 6, a controller 7, a power supply 8, a voltmeter 9 and an ammeter 10. In this embodiment, the electrophoresis apparatus 1 performs component separation by a capillary electrophoresis method. In FIG. 1, in order to simplify the explanation, the power supply 8, voltmeter 9 and ammeter 10 are omitted.

The storage tank 2 comprises a migration solution tank 11, a purified water tank 12 and a cleaning solution tank 13.

Migration solution L1 is stored in the migration solution tank 11. The migration solution L1 is a fluid that functions as a so-called buffer in the capillary electrophoresis method, and, for example, is a 100 mM malic acid arginine buffer (pH 5.0)+1.5% chondroitin sulfate C sodium. Purified water L2 is stored in the purified water tank 12. Cleaning solution L3 is stored in the cleaning solution tank 13.

The dispensing unit 3 inserts a specimen Sp into a capillary flow channel 47 for which capillary electrophoresis is performed, and further has the function of diluting the specimen to a state appropriate for analysis. The dispensing unit 3 comprises a specimen container 14, a dilution tank 15, a syringe 16 and a nozzle 17.

The specimen container 14 comprises a glass blood-collection tube 18, and a cover 60 that is attached to the opening of the blood-collection tube 18. A whole-blood specimen Sp is housed in the blood-collection tube 18. The dilution tank 15 is provided for diluting the specimen Sp to a density suitable for analysis. The nozzle 17 is connected to the syringe 16. The tip end of the nozzle 17 is cut diagonally so that it has a sharp shape in order that it can easily pass through the cover 60. The nozzle 17 can take in and discharge the specimen by the intake or discharge operation of the syringe 16. The nozzle 17 is supported by a drive mechanism that is not illustrated in the figure. Through the action of this drive mechanism, the nozzle 17 can be inserted to or removed from the specimen container 14, can be inserted into or removed from the dilution tank 15, and can be inserted into or removed from the capillary flow channel 47.

The microchip 4 is a member that forms the capillary flow channel 47, and for example, is made of silica. Preferably, the cross-section of the capillary flow channel 47 is round having a 25 to 100 μm diameter, or is rectangular with side lengths being 25 to 100 μm; however, the shape is not limited to this as long as the shape and dimensions are suitable for performing the capillary electrophoresis method.

An inlet hole 19 is formed on one end of the capillary flow channel 47, and a discharge hole 20 is formed on the other end of the capillary flow channel 47. The specimen Sp, migration solution L1, purified water L2 and cleaning solution L3 are filled into the capillary flow channel 47 from the inlet hole 19. The specimen Sp, migration solution L1, purified water L2 and cleaning solution L3 that are filled into the capillary flow channel 47 are discharged from the discharge hole 20.

An electrode 21 is formed on one end of the capillary flow channel 47, and an electrode 22 is formed on the other end. The electrode 21 is exposed from the inlet hole 19, and the electrode 22 is exposed from the discharge hole 20.

The detection unit 5 is provided in order to analyze a certain component that is separated from the specimen inside the capillary flow channel 47, and is located closer to the side of the discharge hole 20 of the capillary flow channel 47 than the inlet hole 19. The detection unit 5 comprises a light source (omitted in the figure) and a light-receiving unit (omitted in the figure), and irradiates the specimen Sp with the light from the light source, and receives reflected light from the specimen Sp by way of the light receiving unit. In doing so, the light absorbance of the specimen Sp is measured.

The controller 7 is provided in order to control all of the parts of the electrophoresis apparatus 1. The controller 7 comprises a control unit 23, an external memory unit 24, main memory unit 25 and an input/output unit 26.

The control unit 23 comprises a CPU (Central Processing Unit) and the like, and executes processing related to electrophoresis component separation according to a program that is stored in the external memory unit 24.

The external memory unit 24 comprises a non-volatile memory such as a flash memory, hard disk, DVD-RAM (Digital Versatile Disc Random-Access Memory), DVD-RW (Digital Versatile Disc ReWritable). The external memory unit 24 stores in advance a program for causing the control unit 23 to perform processing, and stores data supplied from the control unit 23, or supplies stored data to the control unit 23 according to instructions from the control unit 23.

The main memory unit 25 comprises a RAM (Random-Access Memory) or the like. The main memory unit 25 loads the program that is stored in the external memory 24 and is used as a work area for the control unit 23.

The input/output unit 26 comprises an input/output interface, and makes it possible to transmit and receive signals between each part of the electrophoresis apparatus 1 and a PC (Personal Computer) 27 as the information display unit illustrated in FIG. 2.

The temperature adjustment unit 6 is able to adjust the temperature of the microchip 4 by cooling or heating the microchip 4 according to control from the controller 7.

Three-way valves 28, 29, 30, 31 are provided in the electrophoresis apparatus 1. The three-way valves 28, 29, 30, 31 each have three connection ports (omitted in the figure), and the controller 7 controls the connected or disconnected state between these connection ports.

The migration solution tank 11 is connected to the three-way valve 28 via the flow channel 32. The purified water tank 12 and cleaning solution tank 13 are connected to the three-way valve 30 via the flow channels 33 and 34. The dilution tank 15 is connected to the three-way valve 28 via the flow channel 35, and is connected to the three-way valve 31 via the flow channel 36. The three-way valve 28 is connected to the three-way valve 29 via the flow channel 37. The three-way valve 30 is connected to the three-way valves 29 and 31 via the branched flow channel 38.

The inlet hole 19 of the capillary flow channel 47 is connected to the three-way valve 29 via the flow channel 39. A pinch valve 40 is provided in the downstream portion of the flow channel 39 that is connected to the inlet hole 19 of the capillary flow channel 47. The opening and closing of the pinch valve 40 is controlled by the controller 7, which makes it possible to allow or block the flow of fluid into the capillary flow channel 47.

The discharge hole 20 of the capillary flow channel 47 is connected to the three-way valve 31 via the flow channel 41. A pinch valve 56 is provided in the upstream portion of the flow channel 41 that is connected to the discharge hole 20 of the capillary flow channel 47. The opening and closing of the pinch valve 56 is controlled by the controller 7, which makes it possible to allow or block discharge of fluid from the capillary flow channel 47.

A flow channel 42 is provided on the downstream side of the three-way valve 31. The discharge port of the flow channel 42 is located inside a waste fluid bottle 43. The waste fluid bottle 43 is provided in order to store used fluid. A suction pump 44 is connected to the waste fluid bottle 43. The suction pump 44 generates negative pressure according to control from the controller 7. This negative pressure acts on the capillary flow channel 47 from the three-way valve 31 via the branched flow channel 38 and flow channel 41.

As illustrated in FIG. 2, the electrodes 21 and 22 are connected to the power supply 8 via power line 45. A switch 46 is provided between the power supply 8 and electrode 21. Turning ON and OFF of the switch 46 is controlled by the controller 7, and through this control, voltage can be applied from the power supply 8 to the electrodes 21, 22. In the explanation below, an example of a power supply 8 is explained where voltage is applied so that the electrode 21 is a positive electrode and electrode 22 is a negative electrode; however, the power supply 8 can also have the function of applying voltage so that the electrodes are opposite of this.

The voltmeter 9 measures the value of the voltage applied from the power supply 8 to the electrodes 21, 22. The ammeter 10 measures the value of the electric current that flows between the electrodes 21, 22. The measured values from the voltmeter 9 and ammeter 10 are outputted to the controller 7.

Figure 3:
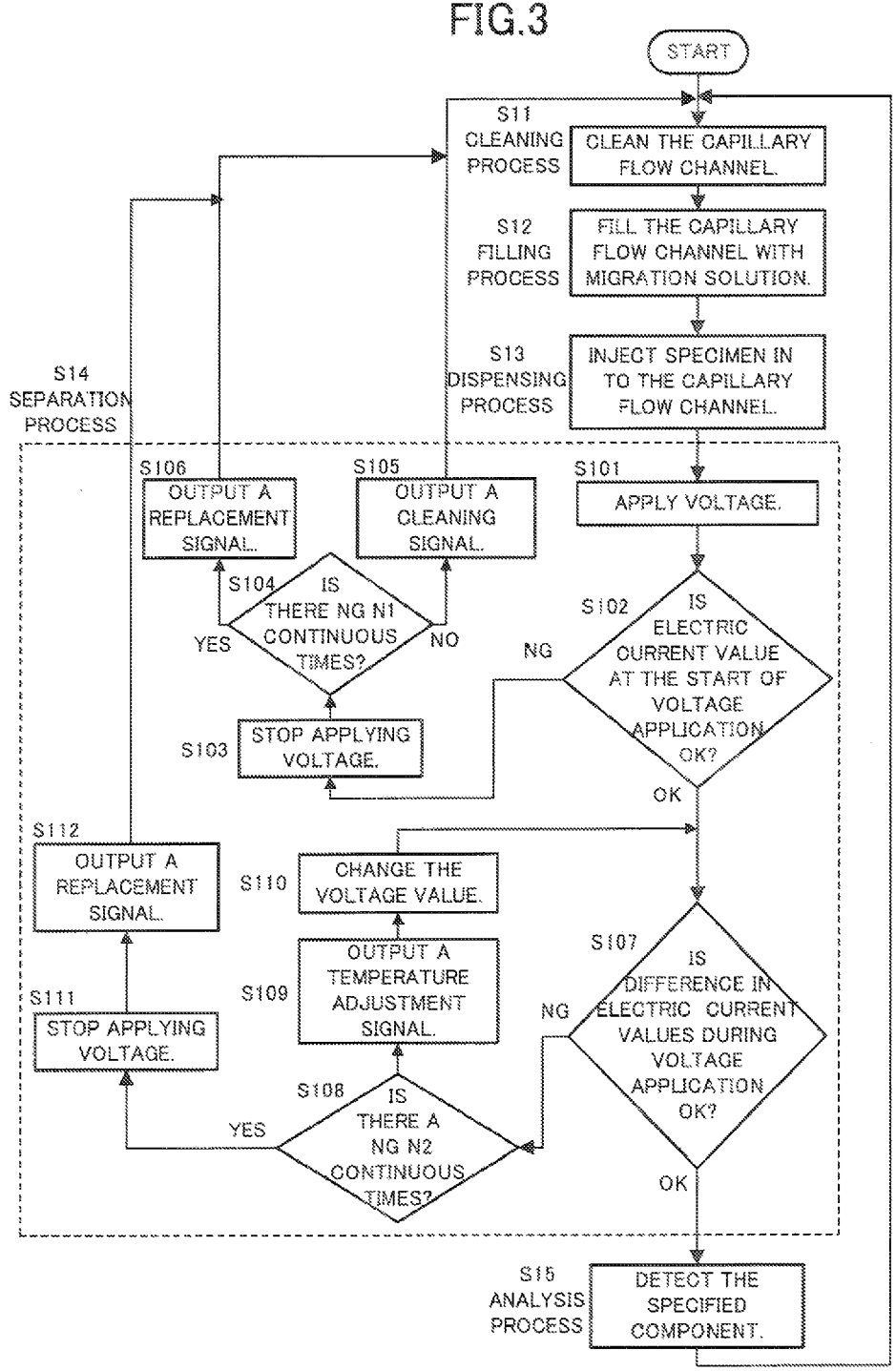
FIG. 3 is a flowchart illustrating the processing that is executed by the electrophoresis apparatus of the first embodiment.

Next, processing that is executed by the electrophoresis apparatus 1 will be explained. FIG. 3 is a flowchart illustrating the processing that is executed by the electrophoresis apparatus 1. The flow of this processing is mainly divided into a cleaning process S11, filling process S12, dispensing process S13, separation process S14 and analysis process S15.

The cleaning process S11 is a process of cleaning the capillary flow channel 47. More specifically, according to a signal from the controller 7, the three-way valve 30 is switched to a state wherein the flow channels 33 and 34 are opened up to the branched flow channel 38. The three-way valve 29 is switched to a state where the branched flow channel 38 is opened up to the flow channel 39. The pinch valve 40 is in the open state, and the pinch valve 56 is in the closed state. The three-way valve 31 is switched to a state wherein the branched flow channel 38 is opened up to the waste fluid bottle 43. In the state above, the controller 7 causes the suction pump 44 to operate and create a negative pressure. As a result of generating this negative pressure, purified water L2 and cleaning solution L3 fill into the capillary flow channel 47, and the filled purified water L2 and cleaning solution L3 are discharged into the waste fluid bottle 43. This cleaning process S11 can also be performed so that purified water L2 is caused to flow through the capillary flow channel 47 after the cleaning solution L3 has flowed through.

The filling process S12 is a process of filling the capillary flow channel 47 with migration solution L1 in order to perform electrophoresis. More specifically, according to a signal from the controller 7, the three-way valve 28 is switched to a state wherein the flow channel 32 is opened up to the flow channel 37, and so that flow channels 32 and 37 are cut off from flow channel 35. The three-way valve 29 is switched to a state wherein the flow channel 37 is opened up to the flow channel 39, and the flow channels 37 and 39 are cut off from the branched channel 38. The pinch valves 40, 56 and the three-way valve 31 are maintained in the same state as in the cleaning process S11. In the state above, by the controller 7 causing the suction pump 44 to operate, the migration solution L1 is filled into the capillary flow channel 47 through the inlet hole 19.

The dispensing process S13 is a process of injecting the specimen Sp into the capillary flow channel 47 from the inlet hole 19.

More specifically, according to a signal from the controller 7, the drive mechanism described above (omitted from the figure) operates and causes the nozzle 17 to penetrate through the cover 60, and the tip end of the nozzle 17 is inserted into the specimen Sp inside the blood-collection tube 18. Then, by the controller 7 causing the syringe 16 to perform the intake operation, the specimen Sp is drawn into the nozzle 17.

On the other hand, by the controller 7 switching the three-way valve 28 to a state wherein the flow channel 32 is opened up to the flow channel 35 and causing the pump (not illustrated in the figure) to generate pressure, migration solution L1 is introduced into the dilution tank 15. Next, by the controller 7 causing the drive mechanism described above to operate, the nozzle 17 is removed from the cover 60, and the tip end of the nozzle 17 is placed into the migration solution L1 in the dilution tank 15. Then, by the controller 7 causing the syringe 16 to perform the discharge operation, the specimen Sp is introduced into the dilution tank 15. At this time, in order to promote mixing of the specimen Sp and the migration solution L1, it is preferred that the intake operation and discharge operation of the syringe 16 be performed repeatedly. The specimen Sp is whole blood that contains hemoglobin, for example. The migration solution L1 contains a hemolytic component that promotes a hemolytic action that breaks down the blood cell membrane, and by mixing the migration solution L1 with the specimen Sp inside the dilution tank 15, the blood cells in the specimen Sp undergo hemolysis.

Next, by the controller 7 causing the syringe 16 to perform the intake operation, the specimen Sp that was diluted in the dilution tank 15 is drawn into the nozzle 17. Then, by causing the drive mechanism described above to operate, the tip end of the nozzle 17 enters into the inlet hole 19 of the capillary flow channel 47. In this state, by the controller 7 causing the syringe 16 to perform the discharge operation, the diluted specimen Sp is introduced into the inlet hole 19. When there is no need for the specimen Sp that is being analyzed to be diluted, it is possible to perform the dispensing process S13 without going through the dilution process.

The separation process S14 is a process of separating out the hemoglobin that is a specified component included in the specimen Sp that is filled into the capillary flow channel 47.

More specifically, in the circuit illustrated in FIG. 2, according to a signal from the controller 7, switch 46 is switched to the ON state, and voltage is applied from the power supply 8 to the electrodes 21, 22 (step S101: FIG. 3). When doing this, the output value from the power supply 8 is adjusted so that the measured value from the voltmeter 9 becomes a specified value. By voltage being applied to the electrodes 21, 22, electric current flows between the electrodes 21, 22, and electroosmotic flow occurs in the fluid inside the capillary flow channel 47 (mixed migration solution L1 and specimen Sp) going from electrode 21 toward electrode 22. As a result, movement occurs in the hemoglobin according to a unique amount of electrophoretic mobility. The electrophoretic mobility differs depending on the substance, so the hemoglobin moves from electrode 21 toward electrode 22 at a different speed than the other components included in the specimen Sp.

The analysis process S15 is a process of detecting the amount or density of hemoglobin, which is a specified component that has been separated out. More specifically, according to a signal from the controller 7, the detection unit 5 irradiates light having a wavelength of 415 nm from the light source described above (omitted in the figure), and then receives the reflected light by way of the light-receiving unit described above. When the hemoglobin that is separated from the specimen Sp passes through the portion of irradiated light from the light source above (black circle portion in FIG. 1), the light absorbance that is found from the state of received light by the light-receiving unit above changes. The amount or density of the hemoglobin is detected by the controller 7 processing this change. The detected amount is stored in the external memory unit 24 of the controller 7 as the analysis result of component separation by electrophoresis.

The electrophoresis apparatus 1 of this embodiment repeats the processing illustrated in FIG. 3, and performs electrophoretic separation of the specimen Sp a plurality of times, so it is possible to put migration solution L1 and specimen Sp into the capillary flow channel 47 and apply voltage to the electrodes 21, 22 a plurality of times.

Here, during the process of repeatedly executing the processing in FIG. 3, by mixing the migration solution L1 and specimen Sp inside the capillary flow channel 47 in each dispensing process S13, the electrical resistance of the fluid inside the capillary flow channel 47 changes.

In the dispensing process S13, due to the work of injecting the specimen Sp into the capillary flow channel 47, or in other words, due to the work of inserting the nozzle 17 into the inlet hole 19 and discharging specimen Sp from the nozzle 17, air bubbles occur and foreign matter mixes in with the fluid inside the capillary flow channel 47. This also causes the electrical resistance of the fluid inside the capillary flow channel 47 to change.

In the separation process S14, by voltage being applied to the electrodes 21, 22 (step S101), Joule heat is stored in the microchip 4, and the temperature of the microchip 4 rises. Due to this rise in temperature, the fluid (mixture of migration solution L1 and specimen Sp) inside the capillary flow channel 47 is heated and the electrical resistance changes. Moreover, as the temperature of the environment where the microchip 4 is located changes, the temperature of the fluid inside the capillary flow channel 47 changes, and thus the electrical resistance also changes.

Due to the change in the electrical resistance described above, the expected electric current does not flow between the electrodes 21, 22, and in order to prevent electrophoretic separation from being performed in this state, the determination process of steps S102 to S112 is executed in the separation process S14. In the determination process of steps S102 to S112, an electrical quantity that occurs in the capillary flow channel 47, or in other words, the value of the electric current that flows between the electrodes 21, 22 (value measured by the ammeter 10) is used.

As illustrated in FIG. 2, in order to execute the determination process in steps S102 to S112, the controller 7 comprises a physical quantity acquisition unit 71, physical quantity determination unit 72, memory unit 73, cleaning determination unit 74, replacement unit 75, temperature adjustment unit 76, voltage change unit 77 and voltage calculation unit 78.

The physical quantity acquisition unit 71, physical quantity determination unit 72, memory unit 73, cleaning determination unit 74, replacement unit 75, temperature adjustment unit 76, voltage change unit 77 and voltage calculation unit 78 are realized by the control unit 23 executing processing according to a program stored in the external memory unit 24. The memory unit 73 is maintained as a structural element of the memory area in part of the main memory unit 25.

The determination processing of steps S102 to S112 includes a determination process that is executed at the point in time when the voltage begins to be applied in step S101 (steps S102 to S106: hereafter referred to as the determination process at the start of voltage application), and a determination process that is executed during the time between when voltage application is started until analysis of the specimen Sp (detection of the amount and density of hemoglobin) is complete (steps S107 to S112: hereafter referred to as the determination process during voltage application).

In the determination process at the start of voltage application, whether or not the electric current value that was measured by the ammeter 10 at the start of voltage application is within a specified range is determined (step S102). When it is determined that the value of the electric current is not within a specified range (step S102: NG), the application of voltage to the electrodes 21, 22 is stopped (step S103). After that, a cleaning signal for cleaning the capillary flow channel 47 is outputted (step S105), and the cleaning process S11 is executed. The object of this process is to stop the separation process S14 in the case where the expected electric current does not flow between the electrodes 21, 22 due to air bubbles being generated or foreign matter being mixed in the fluid inside the capillary flow channel 47, a rise in temperature of the microchip 4, or a change in the temperature of the environment. Furthermore, the object of this process is to remove air bubbles or foreign matter from within the capillary flow channel 47 by cleaning the inside of the capillary flow channel 47.

The determination of step S102 is executed every time voltage is applied in step S101. Moreover, every time NG is determined in step S102, voltage application is stopped (step S103), and a cleaning signal is outputted (step S105).

When determining NG in step S102 continues and determination is repeatedly performed a first set number of times (hereafter this will be taken to be $N_1$ times), after the application of voltage has been stopped, YES is determined in step S104. In this case, a cleaning signal is not outputted; however a replacement signal to replace the microchip 4 is outputted (step S106). The object of this process is to replace the microchip 4 when it is not possible to remove foreign matter that is mixed in the capillary flow channel 47 during cleaning in step S105, or when it is the end of the life of the microchip 4.

In the following, a detailed example of control by the determination process at the start of voltage application will be explained using FIG. 4. In the explanation below, it is presumed that in the case where a NG determination occurs in step S102 continuously and determination is repeated four times (if $N_1$ is four times), YES will be determined in step S104.

Figure 4:
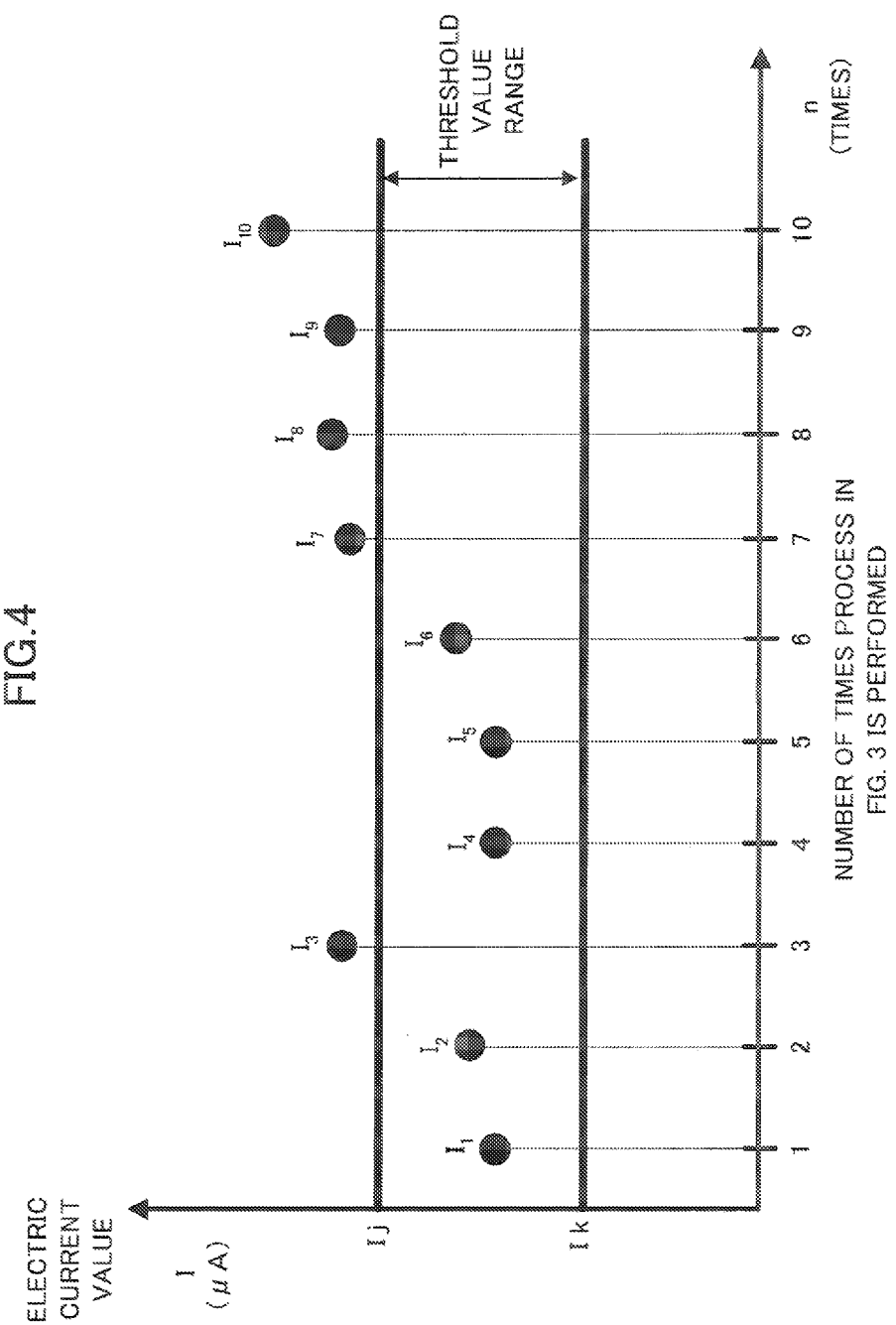
FIG. 4 is a diagram illustrating threshold values (range of electric current values) used in determination of the electric current value in the determination process at the start of voltage application.

FIG. 4 is a diagram illustrating the threshold values that are used in the determination in step S102. The values of electric current $I_1$ to $I_{10}$ that are indicated by black dots are electric current values that are obtained from the ammeter 10 on the first to tenth times when repeating the processing in FIG. 3. The threshold values are set within a range of electric current values of no less than Ik and no greater than Ij. The threshold values above are values that result in desired values of electrophoretic mobility of hemoglobin when electric current within this range flows between the electrodes 21, 22.

The electric currents $I_1$, $I_2$ that are acquired the first and second times are within the range of threshold values. Therefore, in the first and second processing, OK is determined in step S102 (FIG. 3), and processing advances to step S107 that will be described later.

The electric current $I_3$ that is acquired the third time is not within the range of threshold values. Therefore, in the third processing, NG is determined in step S102, and application of voltage is stopped (step S103).

Up to the third time, the number of times that it has been determined that the value of the electric current is not within the range of threshold values (NG in step S102) is only one time (NG on the third time), so that processing does not continue a fourth time. Therefore, in the third time, NO is determined in step S104, and a cleaning signal is outputted (step S105).

The electric currents $I_4$, $I_5$, $I_6$ that are acquired in the fourth, fifth and sixth times are within the range of threshold values. Therefore, in the fourth, fifth and sixth processing, OK is determined in step S102 as in the first and second times, and processing advances to step S107.

The electric currents $I_7$, $I_8$, $I_9$ acquired in the seventh, eighth and ninth times are not within the range of threshold values. Therefore, in the seventh, eighth and ninth times, NG is determined in step S102, and application of voltage is stopped (step S103).

Up to the ninth time, the number of times that it has been determined that the value of the electric current is not within the range of threshold values (NG in step S102) is three times (NG on the seventh, eighth and ninth times), and processing does not advance to a fourth time. Therefore, in the seventh, eighth and ninth times, NO is determined in step S104, and a cleaning signal is outputted (step S105).

The electric current $I_{10}$ that is acquired in the tenth time is also not within the range of threshold values. Therefore, in the tenth time as well, NG is determined in step S102, and application of voltage is stopped (step S103).

Up to the tenth time, the number of times that NG has been continuously determined in step S102 is four times (NG in the seventh, eighth, ninth and tenth times). Therefore, YES is determined in step S104, and a replacement signal to replace the microchip 4 is outputted (step S106).

Next, the determination process during voltage application (steps S107 to S112) will be explained. In steps S107 to S112, the electric current that is measured by the ammeter 10 is acquired at specified intervals of time. Each time the electric current value is acquired, the difference between that electric current and the electric current measured in the past is calculated, and it is determined whether that difference exceeds a specified value (step S107).

When the difference between electric current values exceeds a specified value (NG in step S107), a temperature adjustment signal for adjusting the temperature of the microchip 4 is outputted (step S109). The size of the voltage applied to the electrodes 21, 22 is also changed to a corrected value (step S110). The object of this process is to stabilize the electric current near a target value by adjusting the temperature of the microchip 4, or changing the voltage value, when a large change occurs in the electric current that flows between the electrodes 21, 22 due to fluctuation in temperature of the microchip 4 or the like.

When, due to large fluctuation continuously occurring in the electric current values acquired from the ammeter 10, the number of times that NG is continuously determined in step S107 reaches a second specified number of times (hereafter referred to as $N_2$), YES is determined in step S108. In this case, the application of voltage is stopped without outputting a temperature adjustment signal or changing the voltage value (step S111), and a replacement signal for replacing the microchip 4 is outputted (step S112). The object of this process is to stop the separation process S14 and replace the microchip 4 when fluctuation in the temperature of the microchip 4 cannot be suppressed by adjusting the temperature or changing the voltage value.

In the following, a detailed example of control by the determination processing during voltage application will be explained using FIG. 5. In the explanation below, when NG is continuously determined four times in step S107 ($N_2$ is four times), YES is determined in step S108.

Figure 5:
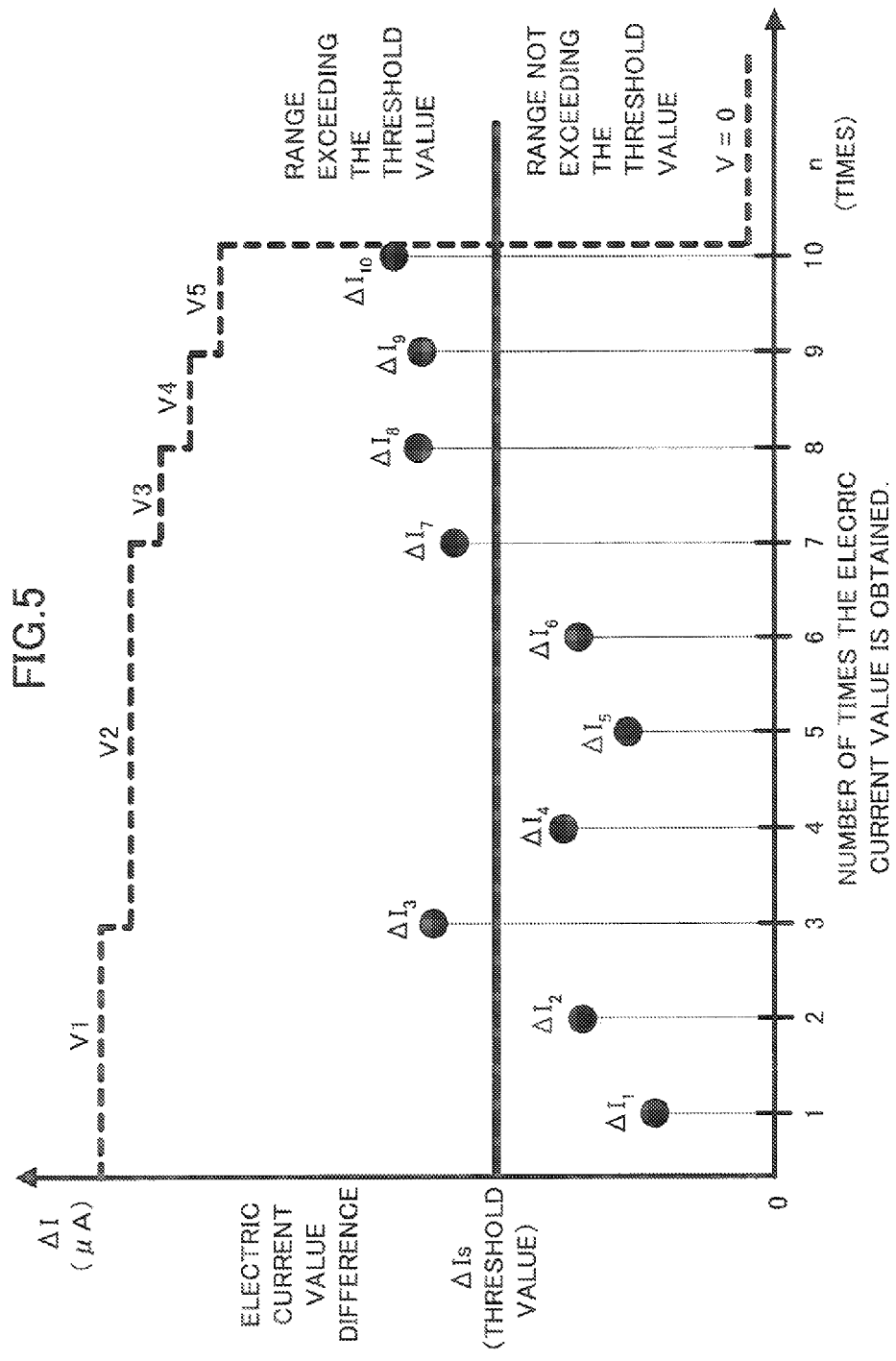
FIG. 5 is a diagram illustrating threshold values (differences in electric current values) used in determination of the difference between electric current values in the determination process during voltage application.

FIG. 5 is a diagram illustrating the threshold value $\Delta I_s$ that is used in the determination of step S107 in the determination process during voltage application.

In the determination process during voltage application, the electric current is acquired from the ammeter 10 at specified intervals as described above. The threshold values $\Delta I_1$ to $\Delta I_{10}$ illustrated in FIG. 5 indicate the differences calculated based on the electric currents acquired in the first to tenth times. The dashed line illustrated in FIG. 5 indicates the fluctuation in the voltage value applied to the electrodes 21, 22.

The differences $\Delta I_1$ and $\Delta I_2$ that were calculated the first and second times do not exceed the threshold value $\Delta I_s$. Therefore, in the first and second times, control such as adjusting the temperature or changing the voltage value in steps S109, S110 is not performed, and the voltage value V1 that is applied in step S101 is maintained.

In the third time, the difference $\Delta I_3$ exceeds the threshold value $\Delta I_s$, so NG is determined in step S107. Up to the third time, the number of times NG is determined is one time (NG in the third time), so that NO is determined in step S108. Therefore, in the third time, a temperature adjustment signal is outputted (step S109), and the voltage value V2 is changed (step S110).

The difference $\Delta I_4$ in the fourth time was calculated with the voltage value being V2, and did not exceed the threshold value $\Delta I_s$. Therefore, in the fourth time, control such as temperature adjustment and changing the voltage value are not performed, and the voltage value V2 is maintained. In the fifth and sixth times as well, the differences $\Delta I_5$, $\Delta I_6$ did not exceed the threshold value $\Delta I_s$, so the voltage value V2 is maintained.

In the seventh, eighth and ninth times, differences $\Delta I_7$, $\Delta I_7$ and $\Delta I_9$ that exceeded the threshold value $\Delta I_s$ were calculated. Therefore, in the seventh, eighth and ninth times, NG is determined in step S107. Up to the ninth time, the number of times that NG was continuously determined in step S107 was 3 times (NG in the seventh, eighth and ninth times). Therefore, in the seventh, eighth and ninth times, by determining NO in step S108, a temperature adjustment signal is outputted (step S109), and in step S110 in the seventh, eighth and ninth times, the voltage value is changed to V3, V4 and V5. The differences $\Delta I_8$ and $\Delta I_9$ in the eighth and ninth times are calculated with the voltage values being V3 and V4.

In the tenth time, the difference $\Delta I_{10}$ is calculated with the voltage value being V5, and the difference $\Delta I_{10}$ exceeds the threshold value $\Delta I_s$. Therefore, in the tenth time as well, NG is determined in step S107. Moreover, the number of times that NG was continuously determined in step S107 is four times (NG in the seventh, eighth, ninth and tenth times). Therefore, in the tenth time, YES is determined in step S108. As a result, application of voltage is stopped (step S111), and a replacement signal to replace the microchip 4 is outputted (step S112).

Figure 6:
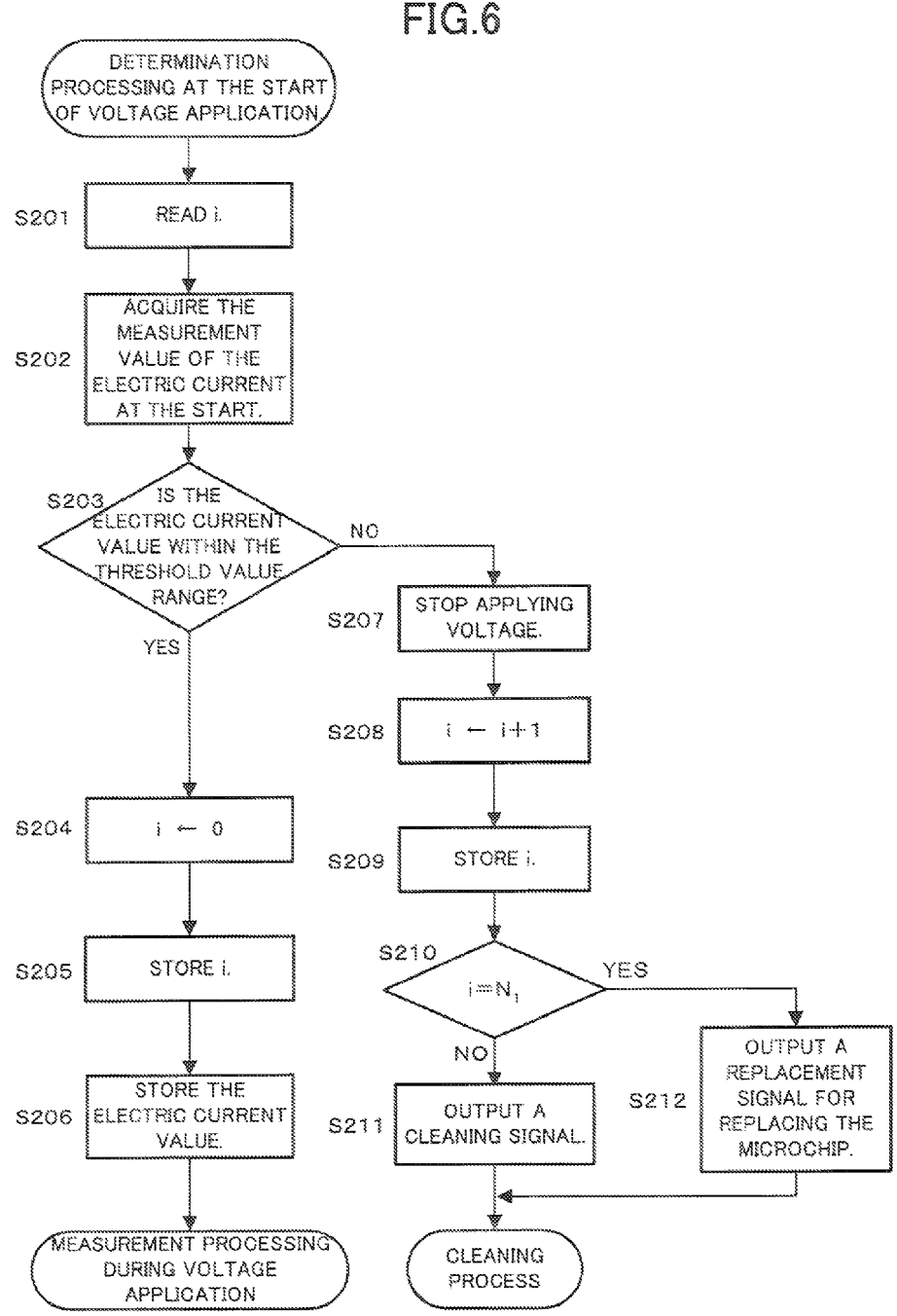
FIG. 6 is a flowchart illustrating the determination process at the start of voltage application.

In the following, the determination processes at the start of voltage application and during voltage application are explained in detail. FIG. 6 is a flowchart illustrating the determination process at the start of voltage application. The processing illustrated in FIG. 6 is started according to the voltage applied in step S101. The processing in FIG. 6 is executed by the physical quantity acquisition unit 71, the physical quantity determination unit 72, memory unit 73, cleaning determination unit 74 and replacement unit 75. In order to execute the processing in FIG. 6, the lower threshold limit Ik and upper threshold value limit Ij illustrated in FIG. 4 are stored in the memory unit 73.

In FIG. 3 and FIG. 6, steps S102 and S203 correspond, steps S103 and S207 correspond, steps S104 and S210 correspond, steps S105 and S211 correspond and steps S106 and S212 correspond.

First, variable i that is stored in the memory unit 73 is read (step S201).

Next, the physical quantity acquisition unit 71 acquires the value of the electric current that is measured by the ammeter 10 at the start of voltage application (step S202).

The physical quantity acquisition unit then determines whether or not the value of the electric current is within the threshold value range (range of no less than electric current Ik and no greater than electric current Ij) (step S203).

When it is determined that the value of the electric current is within the threshold value range (YES in step S203), the variable i is reset to "0" (step S204).

Next, variable i and the electric current value that was acquired in step S202 are stored in the memory unit 73 (steps S205, S206), after which processing advances to the determination process during voltage application (step S107 in FIG. 3).

On the other hand, in step S203, when it is determined that the value of the electric current is not within the threshold value range (NO in step S203), application of voltage to the electrodes 21, 22 is stopped (step S207). More specifically, switch 46 in FIG. 2 is turned OFF.

Next, 1 is added to the variable i (step S208), and variable i is written over and stored in the memory unit 73 (step S209).

Next, whether or not variable i is a specified value $N_1$ is determined (step S210).

When it is determined that variable i is not a specified value $N_1$ (NO in step S210), the cleaning determination unit 74 outputs a cleaning signal (step 211) and the cleaning process S11 (FIG. 3) is executed.

On the other hand, when it is determined that variable i is a specified value $N_1$ (YES is step S210), the replacement unit 75 outputs a replacement signal to the PC 27 (FIG. 2) to replace the microchip 4 (step S212). As a result, an image is displayed on the screen of the PC 27 prompting to replace the microchip 4, and the user is notified that the microchip 4 requires replacement. After the microchip 4 has been replaced, the user operates the electrophoresis apparatus 1, which causes the variable i to be reset to "0", and then causes the cleaning process S11 to begin.

When the processing in FIG. 6 is executed again by repeating the processing in FIG. 3, variable i that was stored in the previous steps S205 and S209 is read in step S201. Depending on the determination result in step S203, either "0" or "1" is added to variable i and the result is stored in steps S205 and S209. In the process of repeating the process in FIG. 3 by reading and storing variable i above, the number of times that NO is continuously determined in step S203 is counted. Each time the processing in FIG. 6 is performed, the determination in step S210 is performed according to the count value above.

Figure 7:
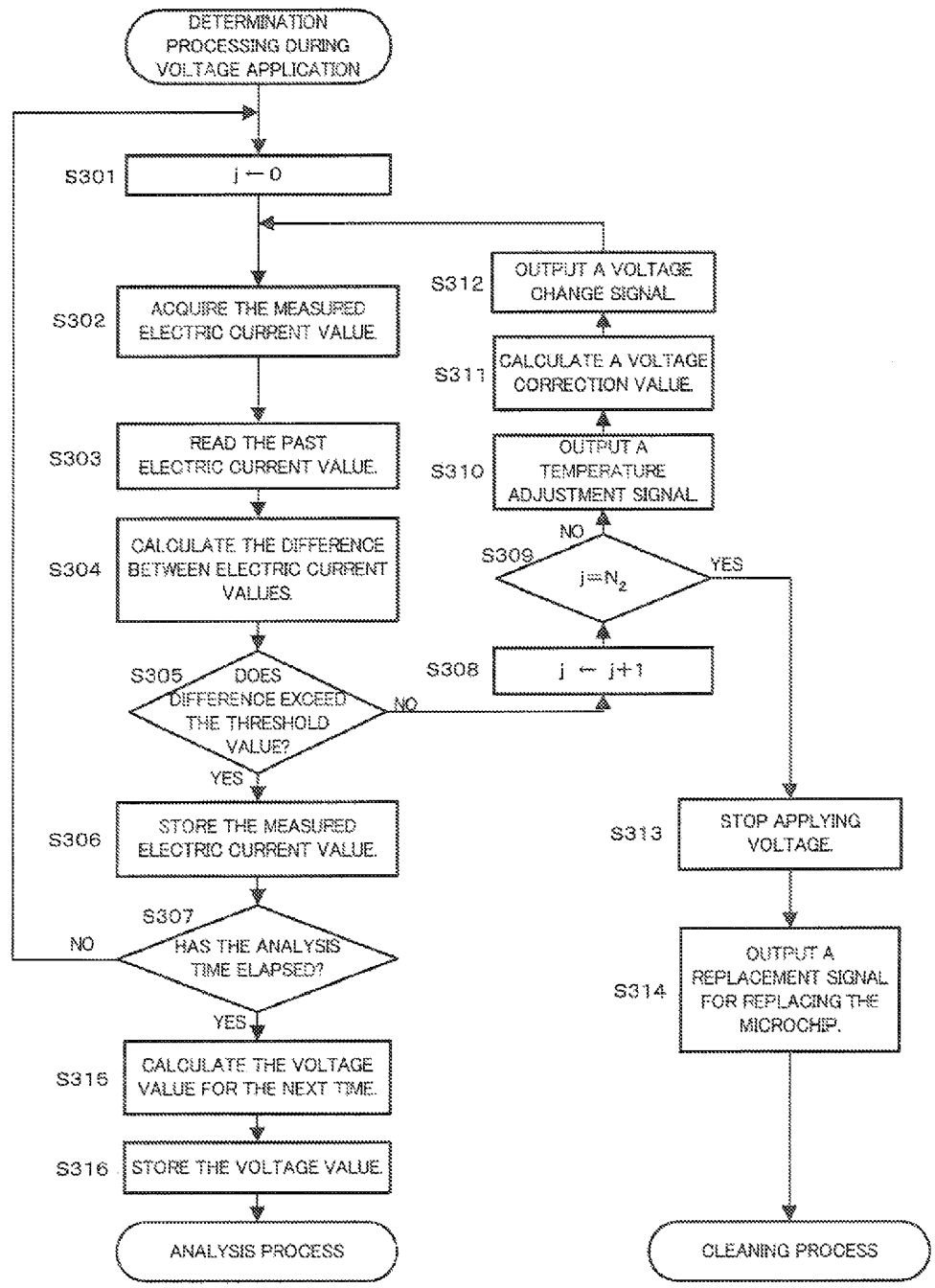
FIG. 7 is a flowchart illustrating the determination process during voltage application.

Next, the determination process during voltage application will be explained in detail. FIG. 7 is a flowchart illustrating the determination process during voltage application. The processing in FIG. 7 is started when the electric current value is stored in the memory unit 73 in step S206 in FIG. 6. The processing in FIG. 7 is executed by the physical quantity acquisition unit 71, physical quantity determination unit 72, memory unit 73, replacement unit 75, temperature adjustment unit 76, voltage change unit 77 and voltage value calculation unit 78. In order to execute the processing in FIG. 7, the threshold value $\Delta I_s$ illustrated in FIG. 5 is stored in the memory unit 73.

In FIG. 3 and FIG. 7, steps S107 and S305 correspond, steps S108 and S309 correspond, steps S109 and S310 correspond, steps S110 and S312 correspond, steps S111 and S313 correspond and steps S112 and S314 correspond.

First, variable j is set to "0" (step S301).

Next, the physical quantity acquisition unit 71 acquires the measured value from the ammeter 10 (step S302). Step S302 is executed at specified intervals, and the processing from step S303 on is executed each time the electric current value is acquired in step S302.

The physical quantity determination unit 72 then reads the electric current value that was stored in the past step S306 (or S206 in FIG. 6) (step S303). In the first time of performing step S303, the electric current value $I_1$ that was stored in step S206 is read.

Next, the physical quantity determination unit 72 calculates the difference between the electric current value acquired in step S302 and the electric current value that was read in step S303 (step S304). When a large change occurred in the electric current that flows between the electrodes 21, 22, a large value is calculated for the difference between electric current values.

The physical quantity determination unit 72 then determines whether or not the difference calculated in step S304 exceeds the threshold value $\Delta I_s$ (step S305).

In step S305, when it is determined that the difference does not exceed the threshold value $\Delta Is$ (YES in step S305), the electric current value that was acquired in step S302 is stored in the memory unit 73 (step S306).

FIG. 8 illustrates a table in which the electric current values are recorded in step S306.

In the table in FIG. 8, electric current value $I_1$ that was stored in step S206 (FIG. 6) is recorded as the initial value, and the electric current values $I_{11}$, $I_{12}$, $I_{14}$, $I_{15}$, $I_{16}$ that were acquired in the first, second, fourth, fifth and sixth time that step S302 was performed are recorded. These values are electric current values whose difference with the electric current values stored in the previous step S306 do not exceed the threshold value $\Delta I_s$.

In the table in FIG. 8, the electric current value acquired in the third time that step S302 was performed is not recorded. This is because the difference $\Delta I_3$ (FIG. 5) between electric current value that was acquired in the third time that step S302 was performed and the electric current $I_{12}$ that was acquired in the second time that step S302 was performed exceeds the threshold value $\Delta I_s$.

Also, for example, the difference $\Delta I_4$ (FIG. 5) between the electric current value $I_{14}$ that was acquired the fourth time that step S302 was performed and the electric current value $I_{12}$ that was acquired the second time that step S302 was performed did not exceed the threshold value $\Delta Is$, so the electric current value $I_{14}$ is not recorded in the table in FIG. 8 (stored in step S306).

After step S306, whether or not the analysis time has elapsed is determined (step S307). The analysis time is the time required from the point when application of voltage is started in step S101 until the hemoglobin passes the portion irradiated with light (block dot portion in FIG. 1). The analysis time, for example, is calculated from the electric current value that is stored in step S306, the electrical mobility of hemoglobin and the length L from the inlet hole 19 to the portion irradiated with light (FIG. 1).

When it is determined that the analysis time has not elapsed (NO in step S307), processing moves to step S301, and processing is repeated from step S301.

In this repeated process, when it is determined in step S305 that the difference exceeded the threshold value $\Delta I_s$ (NO in step S305), processing advances to step S308.

In step S308, 1 is added to variable j, and then in step S309, it is determined whether or not variable j is a specified value $N_2$ (step S309). In other words, each time the electric current value is acquired in step S302, as a result of performing steps S303 to S305, it is determined whether or not the number of times when NO was continuously determined in step S305 has reached $N_2$ times.

When it is determined that the number of times that NO was determined above has not reached $N_2$ (NO in step S309), the temperature adjustment unit 76 outputs a temperature adjustment signal in order to adjust the temperature of the microchip 4 (step S310). By a temperature adjustment signal being input, the temperature regulator 6 (FIG. 1) adjusts the temperature of the microchip 4 by cooling or heating the microchip 4.

Next, the voltage change unit 77 calculates a correction value for the voltage to be applied to the electrodes 21, 22 (step S311). In step S311, first, of the electric current values recorded in the table in FIG. 8, the electric current value recorded most recently is read. For example, during the third time that the processing in FIG. 7 is performed, the electric current value $I_{12}$ from the second time is read. Then, the voltage value that would cause this value $I_{12}$ to flow between the electrodes 21, 22 is calculated as the correction value above. It is also possible to set a target value for the electric current in advance, and to calculate the voltage value that will generate an electric current of this size as the correction value.

The voltage change unit 77 then outputs a voltage change signal in order to change the size of the voltage applied to the electrodes 21, 22 to the correction value in step S313 (step S312). As a result, the value of the voltage that is applied to the electrodes 21, 22 is changed to the correction value that was calculated in step S311.

After that, by moving to step S302, the processing is repeated from step S302.

Through the previous steps S310 to S312, when there is no longer a large change in the electric current that flows between the electrodes 21, 22, in the repeated processing YES is determined in step S305, after which processing moves to step S301 and variable j is reset to "0".

On the other hand, when the change in electric current is not reduced even through the previous steps S310 to S312, NO is determined again in step S305, and 1 is added to variable j (step S308). After that, steps S310 to S312 are executed again, then processing moves to step S302 and the determination in step S305 is performed.

In step S305, when NO is determined repeatedly, 1 is added to variable j each time, and the value of variable j increases.

When the number of times that NO is continuously determined in step S306 reaches $N_2$ and the variable j becomes the specified value $N_2$ (YES in step S309), the switch 46 is switched to OFF, and the application of voltage to the electrodes 21, 22 is stopped (step S313). As a result, the separation process S14 is stopped. Next, the replacement unit 75 outputs a replacement signal for replacing the microchip 4 (step S314). By doing so, an image prompting to replace the microchip 4 is displayed on the screen of the PC 27, and the microchip 4 is replaced. After that, the cleaning process S11 is executed according to operation from the user.

When the processing in FIG. 7 is repeated until YES is determined in step S307 without YES being determined in step S309, the voltage value calculation unit 78 calculates the value of the voltage to be applied in step S101 (FIG. 3) the next time (step S315). In step S315, the voltage value is calculated based on the electric current value that was stored in step S306.

Next, the voltage value that was calculated in step S315 is stored in the memory unit 73 (step S316). The voltage value that is stored in step S316 is read from the memory unit 73 in step S101 the next time, and voltage having this size is applied to the electrodes 21, 22.

With this embodiment, the determination of whether or not the value of the electric current that flows between the electrodes 21, 22 is within a specified range (range of not less than an electric current Ik and no greater than an electric current Ij) (step S203 in FIG. 6) is executed with the migration solution L1 and specimen Sp injected inside the capillary flow channel 47. Therefore, by the character of the fluid inside the capillary flow channel changing due to the migration solution L1 and specimen Sp mixing, by air bubbles being generated in or foreign matter being mixed into the fluid inside the capillary flow channel 47 due to the work of injecting the specimen, by the temperature of the microchip 4 rising, or by the temperature of the environment surrounding the microchip 4 changing, the expected electric current flowing between the electrodes 21, 22 is not detected at the start of voltage application (NO in step S203). Therefore, it is possible to detect abnormality in the capillary flow channel during electrophoretic component separation.

Furthermore, in step S203, when it was determined that the electric current value was not within a specified range (NO in step S203), application of voltage to the electrodes 21, 22 was stopped (step S207), and a cleaning signal was outputted (step S211). Therefore, performing electrophoretic separation with unexpected current flowing is prevented, and fluid inside the capillary flow channel 47 in which air bubbles or the like occurred is replaced.

Moreover, when the temperature of the microchip 4 became high, the electrical resistance of the fluid inside the capillary flow channel 47 changes, and the value of the electric current flowing between the electrodes 21, 22 becomes large. In this case, in the process of repeating the processing in FIG. 6, when the number of times NO is continuously determined in step S203 reaches N1 (YES in step S210), a replacement signal to replace the microchip 4 is outputted (step S212). Therefore, continuously using a hot microchip 4 for electrophoretic separation is avoided.

When the temperature of the microchip 4 greatly changes while voltage is applied to the electrodes 21, 22, in step S305 if FIG. 7 it is determined that the difference between electric current values exceeded the threshold value $\Delta$Is (NO in step S305), and a temperature adjustment signal for adjusting the temperature of the microchip 4 is outputted (step S310). As a result, temperature adjustment of the microchip 4 is performed, so it useful for stabilizing the current flowing between the electrodes 21, 22.

Similar to as described above, when the temperature of the microchip 4 greatly changes while voltage is applied, a voltage change signal is outputted (step S312), and the value of the voltage applied to the electrodes 21, 22 is changed. As a result, even though the temperature of the microchip 4 greatly changes, change in the electric current that flows between the electrodes 21, 22 is kept small.

Moreover, only when it is determined in step S305 that the difference in electric current values does not exceed the threshold value $\Delta$Is (YES in step S305) is the electric current value stored in step S306. In step S312, according to the outputted voltage change signal, the value of the electric current flowing between electrodes 21, 22 is changed to the value stored in the most recent step S306. Therefore, the electric current flowing between the electrodes 21, 22 is controlled to be the value when the difference in step S305 is determined to not exceed the threshold value $\Delta$Is. As a result, the electric current flowing between the electrodes 21, 22 can be controlled to near a target value.

When a large temperature change repeatedly occurs in the microchip 4 while voltage is applied between the electrodes 21, 22, by changing the electric current that flows between the electrodes 21, 22 each time, the difference between the electric current values that is calculated in step S305 becomes large. In this case, when the number of times that NO is continuously determined in step S305 reaches $N_2$ times (YES in step S309), application of voltage is stopped (step S313). Therefore, when it is not possible to suppress temperature fluctuation in the microchip 4 during the temperature adjustment and changing of the voltage value in steps S310 to S312, it is possible to stop the separation process S14 (process that causes electrophoretic separation).

After application of voltage has been stopped in step S313, a replacement signal to replace the microchip 4 is outputted (step S314), prompting replacement of the microchip 4. As a result, continuous use of a microchip 4 in which there was a large temperature change is prevented.

The next time step S101 is performed, the value of the voltage applied to the electrodes 21, 22 is set based on the electric current value that is stored in step S306 (steps S315, S316). As a result, this is useful for controlling the electric current that flows between the electrodes 21, 22 to a value near a target value each time the separation process S14 is performed.

The first embodiment can undergo various variations as described below.

For example, in step S202 in FIG. 6, the instant that the electric current value is acquired is not necessarily limited to being the start of voltage application, and can be set to any arbitrary time while voltage is being applied.

Moreover, in the first embodiment above, the processing in FIG. 6 and FIG. 7 was executed based on the electric current value that was measured by the ammeter 10; however, instead of the electric current value, it is also possible to use the value of the voltage (value measured by the voltmeter 9) applied to the electrodes 21, 22 as the electrical quantity. It is also possible to use the electric power, which is the product of the value of the voltage that is applied to the electrodes 21, 22 and the electric current that flows between the electrodes 21, 22. In the construction in FIG. 2, the measured value from the voltmeter 9 is acquired at the timing that the measured value is acquired from the ammeter 10, and by taking the product of these measured values from the ammeter 10 and voltmeter 9, the amount of electric power can be obtained. When the amount of electric power is used, control is possible that also takes into consideration the fluctuation in the output from the power supply 8.

Furthermore, in the first embodiment above, output of the cleaning signal in step S211 in FIG. 6 is executed every time that NO is determined in step S203; however, it is possible to not output the cleaning signal when the number of times that NO has been determined in step S203 reaches a certain value.

In the first embodiment above, output of the replacement signal in step S212 is executed when the number of times that NO is continuously determined in step S203 reaches $N_1$ times; however, the replacement signal can be outputted when the total number of times that NO is determined in step S203 reaches a certain value.

Moreover, in the first embodiment above, output of the temperature adjustment signal in step S310 in FIG. 7, or output of the voltage correction value calculation and voltage change signal in steps S311 and S312 is executed every time that the difference between electric current values in step S305 was determined to exceed a threshold value (NO in step S305); however, output can also be executed when the number of times that NO is determined in step S306 reaches a certain value.

When NO is determined in step S305, it is possible to execute just one of the output of the temperature adjustment signal in step S310, and the voltage correction value calculation and voltage change signal in steps S311 and S312.

Furthermore, in the first embodiment above, stopping voltage application and outputting a replacement signal in steps S313 and S314 are executed when the number of times that NO is continuously determined in step S305 reaches $N_2$ times; however, this can be executed when the total number of times that NO is determined in step S305 reaches a certain value.

Moreover, the number of capillary flow channels 47 can be set to an arbitrary number. In the case of a plurality of capillary flow channels 47, the processing in FIGS. 3, 6 and 7 is executed for each capillary flow channel 47. The construction of the capillary flow channel 47 is not limited to being a so-called straight type, and could, for example, be a cross-junction type in which two flow channels cross. The specimen Sp is not limited to containing hemoglobin, which is representative of whole blood, and could include, for example, DNA, RNA (rebonucleic acid) or protein.

(Embodiment 2)

Figure 9:
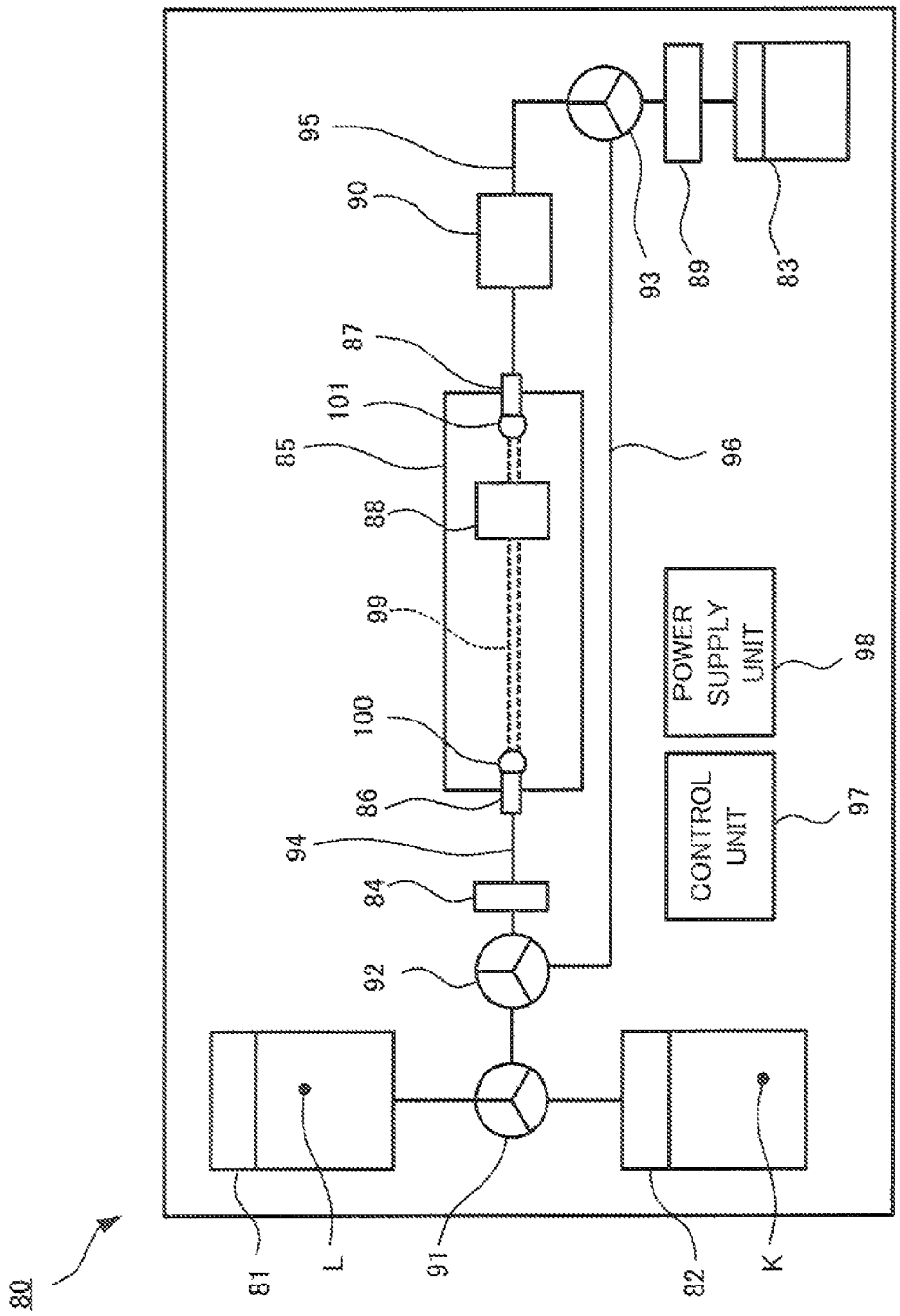
FIG. 9 is a diagram illustrating the construction of the electrophoresis apparatus of a second embodiment of the present invention.

FIG. 9 is a diagram illustrating the construction of an electrophoresis apparatus 80 of a second embodiment of the present invention. The electrophoresis apparatus 80 of this second embodiment comprises: a fluid storage tank 81, specimen tank 82, waste fluid tank 83, dispensing unit 84, microchip 85, electrodes 86, 87, detection unit 88, pump (pressure generation unit) 89, suction pump 90, three-way valves 91 to 93, flow channel 94 to flow channel 96, control unit 97 and power supply 98. The microchip 85 comprises a capillary flow channel 99, inlet hole 100 and discharge hole 101.

Stored fluid L, for example, migration solution, purified water, cleaning solution and the like are stored in the stored fluid tank 81. Specimen fluid K is stored in the specimen tank 82. Specimen fluid K is a sample containing a certain component for which analysis is to be performed by the electrophoresis apparatus 80, and is in a form of being processed in a state suitable for measurement, for example, a diluted or mixed state. Used fluid is stored in the waste fluid tank 83.

The dispensing unit 84 injects the specimen fluid K that is in the specimen tank 82 into the capillary flow channel 99 of the microchip 85.

The pump 89 generates pressure. The pressure that the pump 89 generates is applied to the flow channels 95, 96 via the three-way valve 93. The pump 89 can feed solution into the electrophoresis apparatus 80 that includes the flow channels and functional units.

Figure 10A:
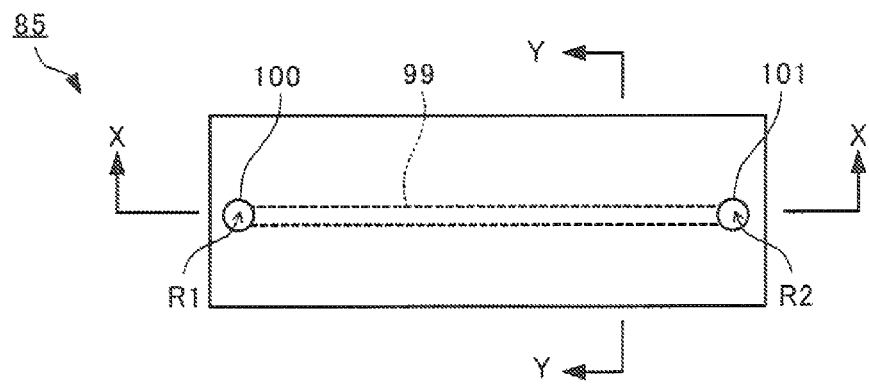
FIG. 10A is a top view illustrating a microchip of the second embodiment.
Figure 10B:
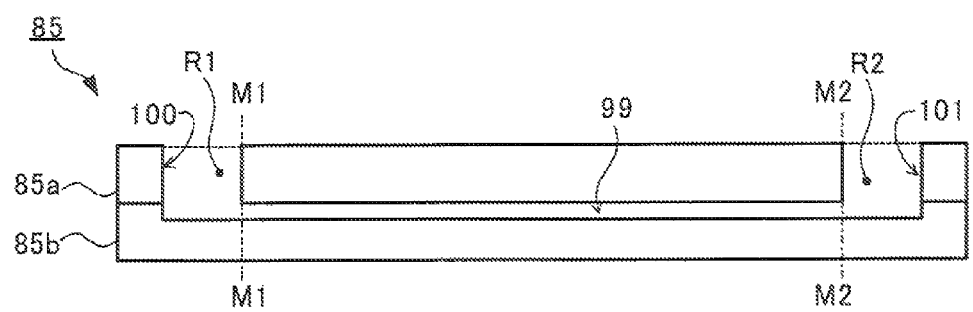
FIG. 10B is a cross-sectional view of section X-X in FIG. 10A of the microchip of the second embodiment.
Figure 10C:
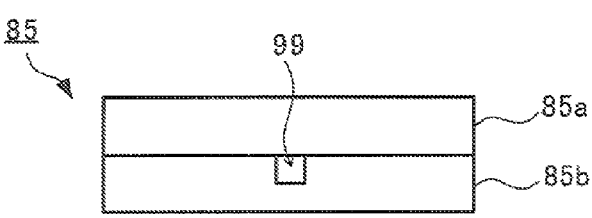
FIG. 10C is a cross-sectional view of section Y-Y in FIG. 10 A of the microchip of the second embodiment.

FIG. 10A is a top view illustrating the microchip 85 of this second embodiment. FIG. 10B is a cross-sectional view of section X-X in FIG. 10A of the microchip 85 of this second embodiment. FIG. 10C is a cross-sectional view of section Y-Y in FIG. 10A of the microchip 85 of this second embodiment.

The microchip 85 has a minute flow channel formed in the substrate thereof that is made of a resin material, and functions as the capillary flow channel 99. The microchip 85 is formed by joining together a substrate 85*a* and a substrate 85*b*. The substrate 85*a* functions as a base where the capillary flow channel 99 is formed. The inlet hole 100 and the discharge hole 101 are formed in the substrate 85*b* at a position that corresponds to the capillary flow channel 99.

In this second embodiment, the cross section of the capillary flow channel 99 is set as a square with each side being 40 μm, and the length of the capillary flow channel 99 is set at about 30 mm. The cross section and length of the capillary flow channel 99 is not limited to the values above.

An inlet hole 100 and discharge hole 101 are formed in the capillary flow channel 99. The inlet hole 100 is provided on one end of the capillary flow channel 99 and the specimen fluid K is input through the inlet hole 100 from the dispensing unit 84. In this second embodiment, in addition to the specimen fluid K, it is possible to input stored fluid L such as migration solution, purified water, cleaning solution and the like to through the inlet hole 100. The discharge hole 101 is provided on the other end of the capillary flow channel 99, and the specimen fluid K and stored fluid L that were filled into the capillary flow channel 99 are discharged from the discharge hole 101.

The spatial portion of the inlet hole 100 that passes through the substrate 85*a* and connects to the capillary flow channel 99 is called reservoir R1. Similarly, the spatial portion on the discharge hole 101 side (the spatial portion of the discharge hole 101 that passes through the substrate 85*a* and the comes in contact with the capillary flow channel 99) is called reservoir R2.

An electrode 86 and electrode 87 are provided on both ends of the capillary flow channel 99. In this second embodiment, the electrode 86 is exposed in the inlet hole 100, and the electrode 87 is exposed in the discharge hole 101.

The detection unit 88 analyzes a specified component that is separated out from the specimen fluid K in the capillary flow channel 99. The detection unit 88 is provided in the portion of the capillary flow channel 99 that is closer to the discharge hole 101 than the inlet hole 100. The detection unit 88 comprises, for example, a light source and a light receiving unit. The detection unit 88 irradiates light from the light source onto the specimen fluid K, and by the light receiving unit receiving the light that passes through, it is possible to measure the light absorption and analyze a specified component.

Figure 11:
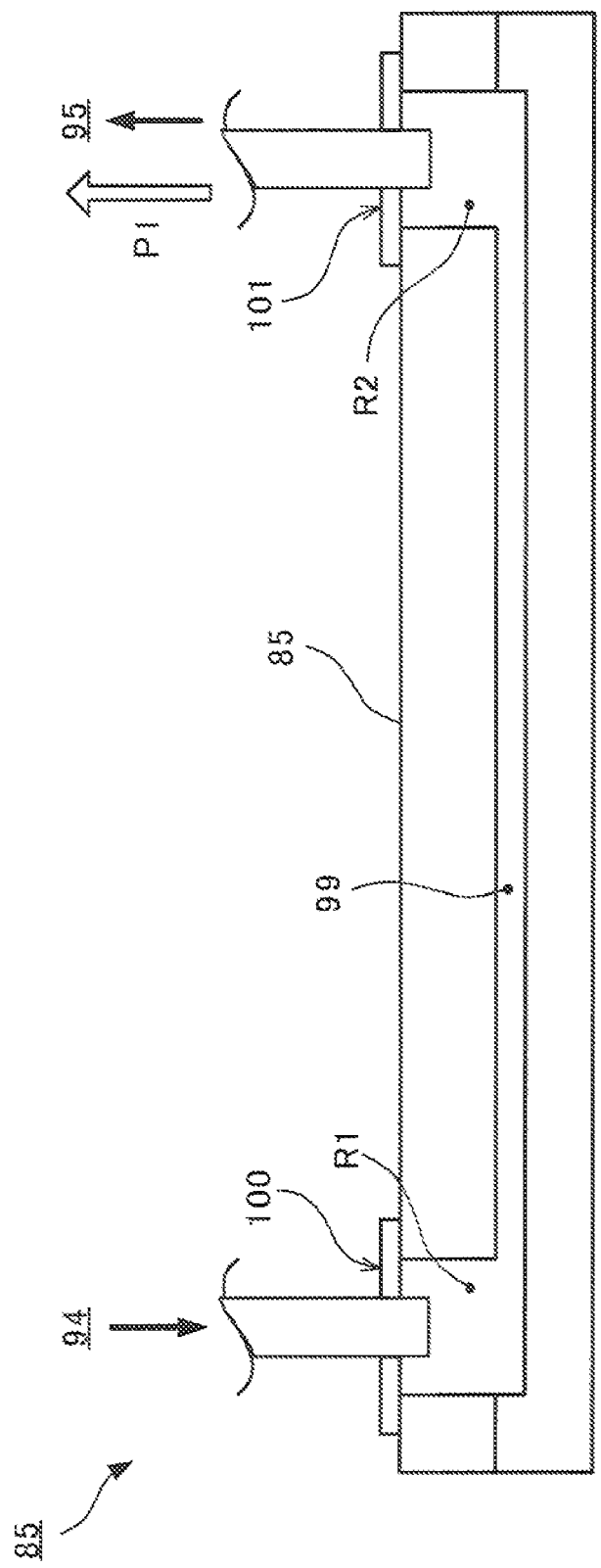
FIG. 11 is a partial view that includes the microchip of the electrophoresis apparatus of the second embodiment.

FIG. 11 is a partial view that includes the microchip 85 of the electrophoresis apparatus of this second embodiment. FIG. 11, similar to FIG. 10B, illustrates the state wherein the microchip 85 has been cut along section line X-X in FIG. 10A.

The suction pump 90 can draw in solution that is in the capillary flow channel 99 from the flow channel 95 side by the suction force P1. When the suction pump 90 is operated, the solution inside the capillary flow channel 99 is drawn toward the flow channel 95 by the suction force P1, and discharged to the waste fluid tank 83.

Suction force P1 is applied by the suction pump 90 and sucks the solution inside the capillary flow channel 99. When doing this, force is applied such that it pulls both the substrate 85*a* and substrate 85*b* of the microchip 85 against each other, and the direction of this force is the same as the direction of the force applied when applying pressure to the substrate 85*a* and substrate 85*b* in order to join together the substrate 85*a* and substrate 85*b*. Therefore, by generating a suction force P1 in the suction pump 90, it is possible to reduce the possibility that the substrate 85*a* and substrate 85*b* will come apart.

It is also possible to have the pump 89 that feeds solution function as the suction pump 90, or in other words, have the pump 89 draw in the solution that is in the capillary flow channel 99. In this case, by controlling the opening and closing of the three-way valve 93, and by generated a suction force P1 in the pump 89 while the flow channel 95 is opened up to the pump 89, the pump 89 functions the same as the suction pump 90. By doing so, it is possible to eliminate the suction pump 90 when designing the electrophoresis apparatus 80.

In order to remove the solution inside the capillary flow channel 99, it is possible to perform purging of the solution instead of suction. Supposing the case of purging the solution inside the capillary flow channel 99, a force applies pressure to the solution in the capillary flow channel 99 from the inside toward the outside. In other words, a force is applied in the direction that promotes the joined surfaces of the substrate 85*a* and substrate 85*b* to come apart, and the load on the microchip 85 becomes large. When sucking out instead of purging the solution inside the capillary flow channel 99, a force is applied that pulls the substrate 85*a* and the substrate 85*b* together, eliminating the possibility of the substrates 85*a*, 85*b* coming apart. Therefore, in order to remove the solution inside the capillary flow channel 99, performing suction instead of purging is preferred.

However, when the solution in the capillary flow channel 99 is sucked from one side and purged from the other side, and the suction force is greater than the purging pressure, a force is applied that pulls the substrate 85a and substrate 85b together. Purging pressure can be used together with the suction force only when purging pressure is applied as an aid when performing this kind of suction.

The operation of the parts of the electrophoresis apparatus 80 described above is controlled by the control unit 97. The control unit 97 comprises a CPU, memory, input/output interface and the like.

Three-way valves 91, 92 are provided in the electrophoresis apparatus 80. The three-way valves 91, 92 each have three connection ports, and the connected state and blocked state of these connection ports are independently controlled by the control unit 97.

The fluid storage tank 81 and specimen tank 82 are connected to flow channel 94 or flow channel 96 via the three-way valves 91, 92. The opening and closing of the three-way valves 91, 92 is controlled by the control unit 97, and the connected state and blocked state with the capillary flow channel 99 are independently controlled. The flow channel 94 is connected to the capillary flow channel 99 of the microchip 85, and the flow channel 96 is connected to the waste fluid tank 83.

As illustrated in FIG. 11, fluid that is input from flow channel 94 to inlet hole 100 (or in other words, the reservoir R1 portion) flows through the capillary flow channel 99 and to the flow channel 95 via the discharge hole 101 (or in other words reservoir R2).

The power supply 98 is connected to electrode 86 and electrode 87, and applies a 1.5 kV voltage to the electrodes 86, 87. For example, the power supply 98 applies a voltage such that the electrode 86 is a positive electrode and electrode 87 is a negative electrode; however, may also have the function to apply voltage so that the polarity is opposite this.

Figure 12:
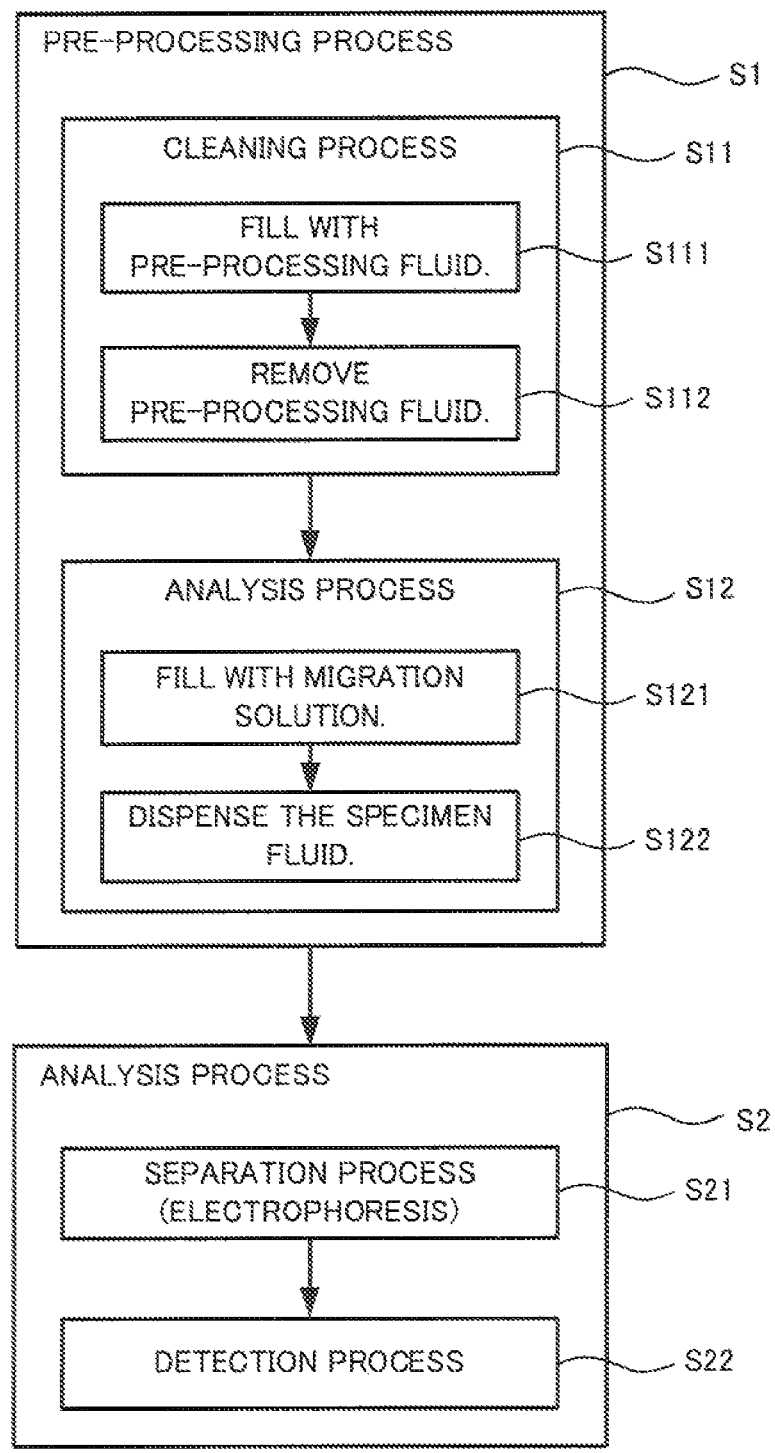
FIG. 12 is a flowchart illustrating the processing executed by the electrophoresis apparatus of the second embodiment.

In the following, FIG. 9 to FIG. 13 will be used to explain the processing that is executed by the electrophoresis apparatus 80 of this second embodiment. FIG. 12 is a flowchart illustrating the processing executed by the electrophoresis apparatus 80. This flow is mainly divided into a pre-processing process (step S1) and an analysis process (step S2).

A cleaning process of the pre-processing equipment (step S11) is a process that is performed first in the pre-processing process (step S1), and when the electrophoresis apparatus 80 is used continuously, is a process that is performed to clean each of the parts of the electrophoresis apparatus 80. After that, the dispensing process for inserting the specimen (step S12) is performed.

More specifically, the cleaning process (step S11) is divided into filling the pre-processing fluid (step S111) and discharging the pre-processing fluid (step S112), and cleaning is performed by causing pre-processing fluid such as cleaning solution or purified water to flow through the inside of the capillary flow channel 99.

Figure 13:
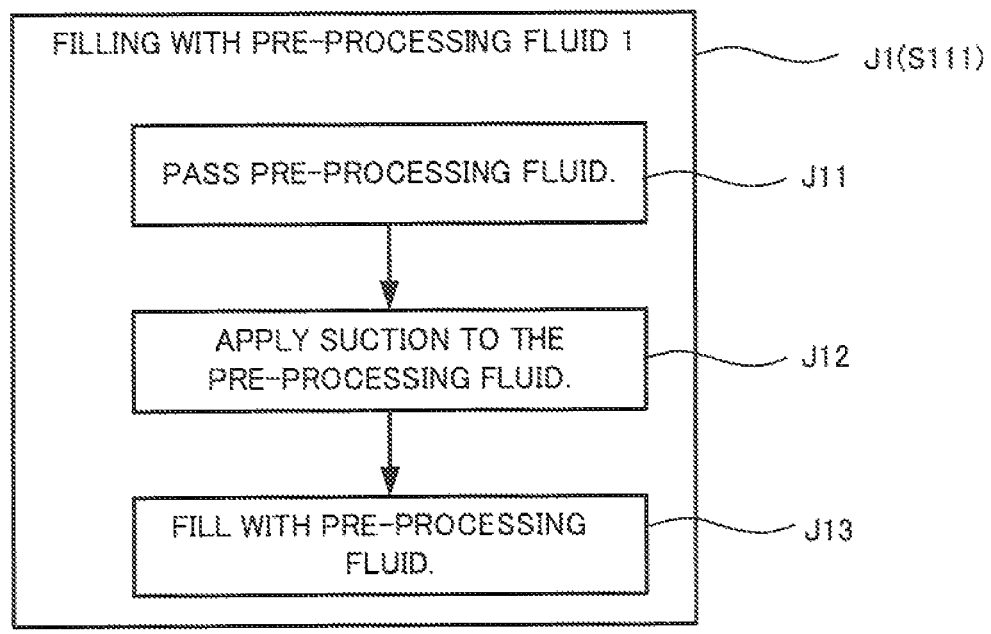
FIG. 13 is a flowchart illustrating part of the cleaning process in pre-processing that is executed by the electrophoresis apparatus of the second embodiment.

In this second embodiment of the present invention, the pre-processing fluid is filled by the following method. FIG. 13 is a flowchart illustrating the process of filling the pre-processing fluid, which is part of the cleaning process of the pre-processing process that is executed by the electrophoresis apparatus 80 of this second embodiment. Filling of the pre-processing fluid (step S111) is explained as filling 1 of pre-processing fluid (step J1).

First, by discharging pre-processing fluid to the flow channel 112 via the discharge hole 101 at the same time that the pre-processing fluid is introduced into the capillary flow channel 99 by way of the flow channel 94 and inlet hole 100, the pre-processing fluid flows through the capillary flow channel 99 (step J11).

Then, the suction pump 90 is used to suck out the pre-processing fluid that is passing through the capillary flow channel 99 with a suction force P1 (step J12). As a result, the pre-processing fluid in the capillary flow channel 99 flows toward the discharge hole 101 with much energy, and by flowing into the reservoir R2, can fill the reservoir R2 with pre-processing fluid. With this passing fluid, the capillary flow channel 99 is filled with the pre-processing fluid, and the reservoir R2 is also filled with pre-processing fluid (step J13). Here, the capillary flow channel 99 can be cleaned by the pre-processing fluid flowing through the capillary flow channel 99. Moreover, with a sufficient amount of pre-processing fluid flowing into the reservoir R2 of the discharge hole 101, the reservoir R2 can be cleaned.

Filling with pre-processing fluid (step S111) ends and again the suction pump 90 is used to apply suction to the capillary flow channel 99 with a suction force P1. The pre-processing fluid in the capillary flow channel 99 cleans away impurities such as specimen K that was used in the previous analysis, and is discharged to the waste fluid tank 83 via the flow channel 112 (step S112). By removing the pre-processing fluid with suction, it is possible to remove all of the pre-processing fluid that remains in the capillary flow channel 99. Therefore, there is no fear of the solution that will be filled into the capillary flow channel 99 next mixing with the pre-processing fluid, and cleaning efficiency is improved.

The dispensing process (step S12) is a processing of filling the capillary flow channel 99 with migration solution for enabling electrophoresis and specimen fluid K. First, the migration fluid is filled into the capillary flow channel 99 (step S121). Next, the dispensing unit 84 injects the specimen fluid K into the capillary flow channel 99, which has been sufficiently filled with migration solution (step S122).

When filling with the migration solution as well (step S121), the suction pump 90 can be used to apply suction as in the case of filling with pre-processing fluid. Even when the capillary flow channel 99 and reservoir R2 are filled with migration solution, by using the suction pump 90 to apply suction, it is possible to completely fill the capillary flow channel 99 and reservoir R2.

After the pre-processing process (step S1) has ended, the analysis process (step S2) is executed. The analysis process (step S2) comprises a separation process (step S21) and a detection process (step S22).

The separation process (step S21) is a process of separating out a specified component contained in the specimen fluid K by electrophoresis. In the separation process (step S21), electrophoresis is performed by putting specimen fluid K into the capillary flow channel 99 that is filled with migration solution and applying voltage to the electrodes 86, 87. In the separation process, by filling the capillary flow channel 99 with migration solution in step S121, it becomes easier to inject the specimen fluid K, and it is possible to perform the separation process (step S21) with better precision.

More specifically, separation by electrophoresis can be achieved by applying voltage from the power supply 8 to the electrodes 86, 87 according to an instruction from the control unit 97 so that the electrode 86 becomes a positive electrode and the electrode 87 becomes a negative electrode, and by generating an electroosmotic flow in the migration solution going from the electrode 86 to the electrode 87. When that happens, movement of the specified component from the electrode 86 to the electrode 87 occurs according to unique electrophoretic mobility.

The detection process (step S22) is a process of detecting the amount or density of a specified component that was been separated out. More specifically, according to an instruction from the control unit 97, the detection unit 88 irradiates light having a wavelength of 415 nm from the light source onto a specified location of the capillary flow channel 99, and the light receiving unit receives the light that passes through. When the specified component passes the specified location of the capillary flow channel 99, the light (light absorbance) received by the light receiving unit changes, and from that change it is possible to detect the density or amount of specified component. The analysis result is stored for example in a memory unit (not illustrated in the figure), and the detection process (step S22) ends. Through the process above, the pre-processing process (step S1) and analysis process (step S2) end, and analysis using the electrophoresis apparatus 80 is completed.

In this second embodiment, the control unit 97 (FIG. 9) functions as the physical quantity acquisition unit 71, physical quantity determination unit 72, memory unit 73, cleaning determination unit 74, replacement unit 75, temperature adjustment unit 76, voltage change unit 77 and voltage value calculation unit 78 illustrated in FIG. 2, and these units execute the steps S101 to S112 in FIG. 3 and the processing in FIG. 6 and FIG. 7. Step S101 in FIG. 3 is the separation process (step S21), and is executed according to the voltage that is applied to the electrodes 86, 87.

Figure 14:
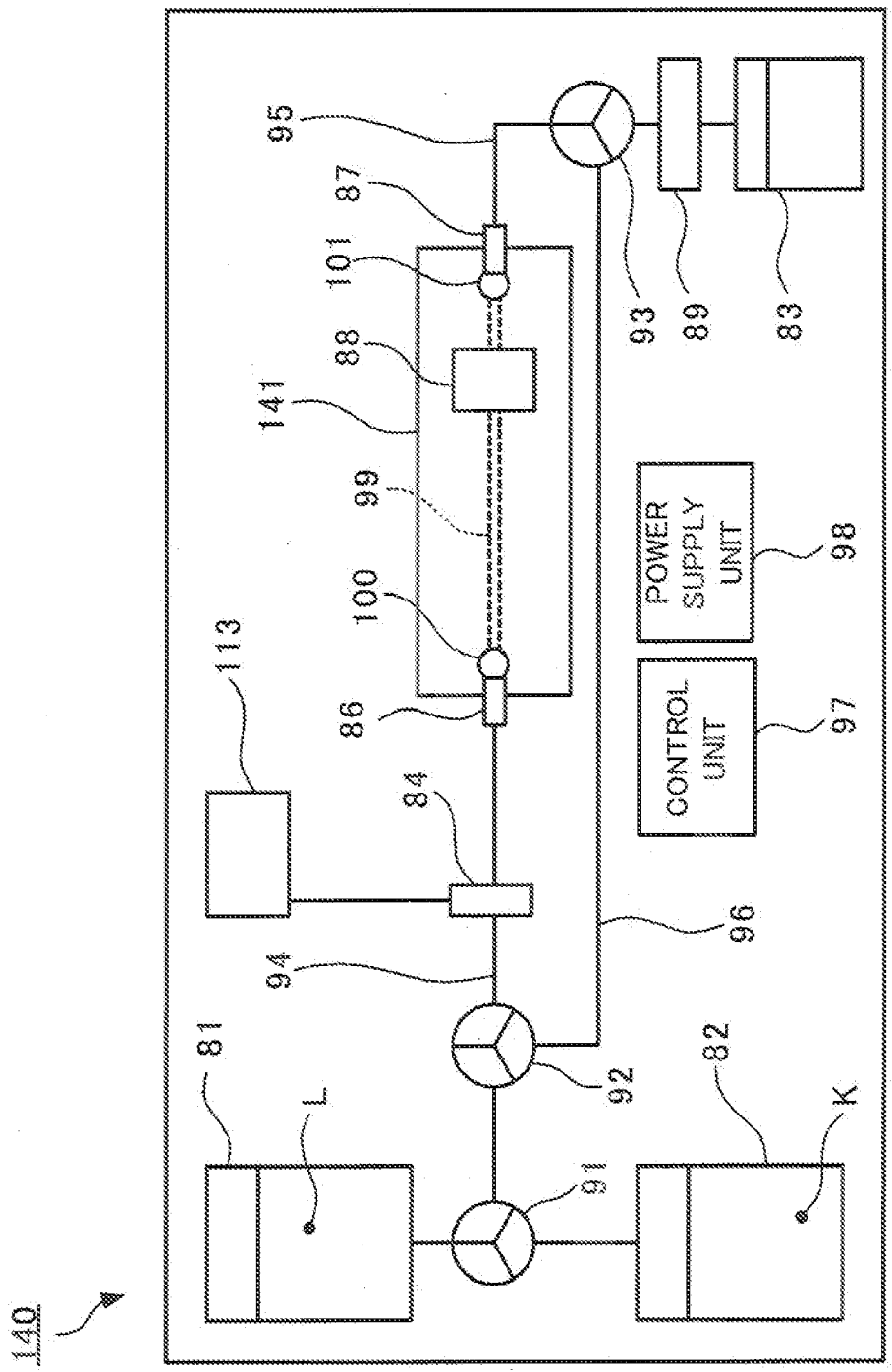
FIG. 14 is a diagram illustrating the construction of an electrophoresis apparatus of a variation of the second embodiment.
Figure 15:
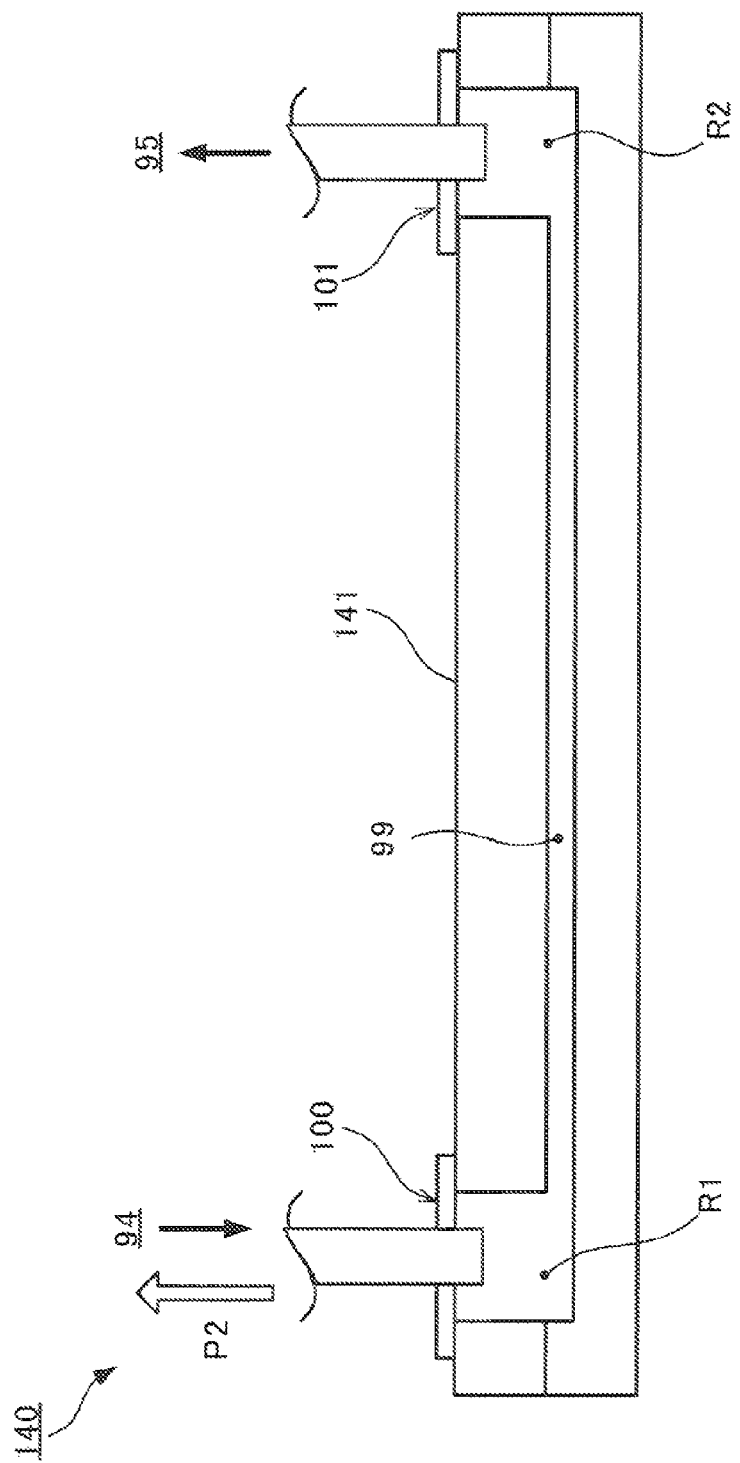
FIG. 15 is a partial view that includes a microchip of the electrophoresis apparatus of a variation of the second embodiment.

FIG. 14 is a diagram illustrating the construction of an electrophoresis apparatus 140 of a variation of embodiment 2. FIG. 15 is a partial view that includes the microchip 141 of the electrophoresis apparatus 140 of a variation of the second embodiment. In this variation of the second embodiment, a suction pump 113 is provided on the inlet hole 100 side. The other construction is the same as the electrophoresis apparatus 80 illustrated in FIG. 9 and FIG. 11.

The suction pump 113 is provided in the flow channel 94. The suction pump 113 removes the stored fluid L and specimen fluid K (collectively referred to as the solution) in the capillary flow channel 99 by sucking out the solution in the capillary flow channel 99 from the inlet hole 100 side with a section force P2.

In this second embodiment, with the pre-processing fluid flowing through the capillary flow channel 99, the pre-processing fluid in the capillary flow channel 99 is sucked out by having the suction pump 113 generate a suction force P2 when the capillary flow channel 99 is filled to a certain extent with the pre-processing fluid. As a result, by sucking the pre-processing fluid toward the flow channel 94, it is possible to fill the pre-processing fluid into the reservoir R1.

When the suction pump 113 generates a suction force and sucks out the pre-processing fluid in the capillary flow channel 99, or in other words, when supply of pre-processing fluid from the flow channel 94 to the capillary flow channel 99 is stopped, the three-way valve 92 is switched according to control from the control unit 97 so that flow channels 94 and 96 are connected. As a result, due to the suction of the suction pump 113, the pre-processing fluid that flowed in the flow channel 94 flows toward the flow channel 96, and finally flows into the waste-fluid tank 83. Similar to removing the pre-processing fluid in the capillary flow channel 99, the three-way valve 92 is switched by the control unit 97 so that the pre-processing fluid flows to the waste-fluid tank 83. When suction by the suction pump 113 ends, the three-way valve 92 is switched by the control unit 97, and the pre-processing fluid flows from the flow channel 94 to the capillary flow channel 99.

It is also possible to have the pump 89 that feeds solution function as the suction pump 113, or in other words, having the pump 89 perform the function of sucking out solution that is in the capillary flow channel 99. In this case, opening and closing of the three-way valves 92, 93 is controlled, and when the flow channels 94, 96 are connected to the pump 89 and the pump 89 generates a suction force P2, the pump 89 functions the same as the suction pump 113. By doing so, it is possible to eliminate the suction pump 113 when designing the electrophoresis apparatus 140.

By performing the process (step J12) of sucking the pre-processing fluid in the capillary flow channel 99 by the suction pump 113 in the filling of pre-processing fluid (step S111) in the cleaning process (step S11), it is possible to completely fill the inside of the reservoir R1 with pre-processing fluid.

Similar to the process of filling with pre-processing fluid, in step S121 as well, filling with migration solution can also be performed by apply suction from a suction pump 90. By doing so, it is possible to more reliably perform filling even when filling the capillary flow channel 99 and reservoir R1 with migration solution.

In this variation of the second embodiment, suction is performed from the inlet hole 100 side via the flow channel 94; however, it is also possible to perform suction from the inlet hole 100 side via a flow channel that is separate and different from the flow channel 94 and that is connected to the inlet hole 100. By doing so, not only is the discharge hole 101 side cleaned, but the inlet hole 100 side is also cleaned, so it is possible to improve the cleaning effect inside the capillary flow channel 99.

As explained above, with this second embodiment, in the pre-processing process (particularly, the cleaning process), it is possible to reduce mechanical load on the flow channel of the microchip, and to improve the cleaning efficiency.

In cleaning of the capillary flow channel and reservoir, it was easy for filling with solution into minute areas to become inadequate, and there were areas where cleaning was not performed; however, but using suction, filling with solution could be performed reliably. As a result, cleaning became thorough, and the cleaning efficiency was improved.

Moreover, by applying suction to the solution flowing in the capillary flow channel, the cleaning efficiency of the capillary flow channel can be improved. Furthermore, by applying suction to the capillary flow channel, and discharging the solution from the capillary flow channel, there is no mixing with the solution to be used next, and thus it becomes possible to improve the cleaning efficiency.

As described above, by improving the cleaning efficiency, the microchip can be maintained in a clean state. Therefore, repeated use during analysis becomes possible, and the number of times the microchip can be used until it is disposed of can be increased.

Furthermore, by applying suction when performing cleaning, it is possible to reduce the burden on the microchip, there is no fear of the joined surfaces of the substrates of the microchip coming apart, and the durability of the microchip is improved. As a result, the microchip can be used repeatedly during analysis, and the number of times the microchip can be used can be increased.

(Embodiment 3)

Figure 16:
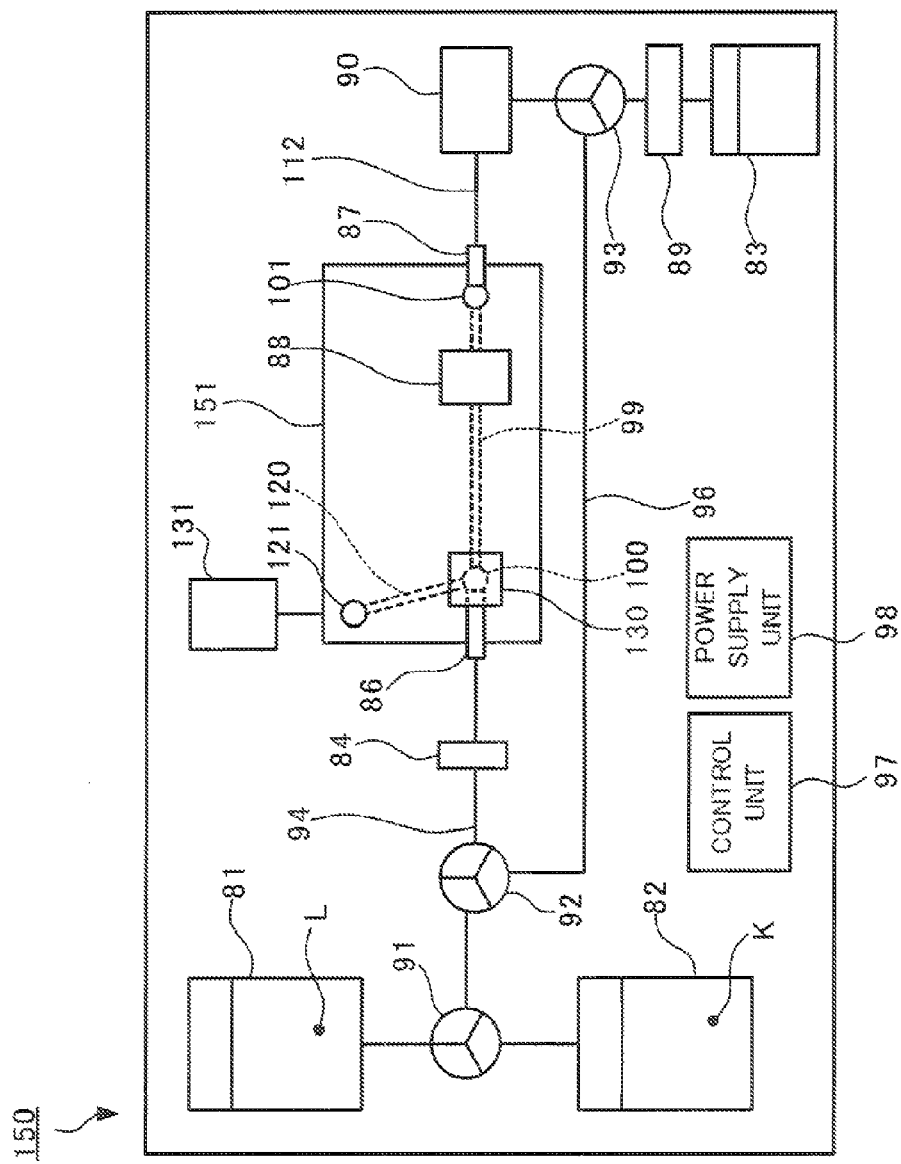
FIG. 16 is a diagram illustrating the construction of an electrophoresis apparatus of a third embodiment of the present invention.
Figure 17:
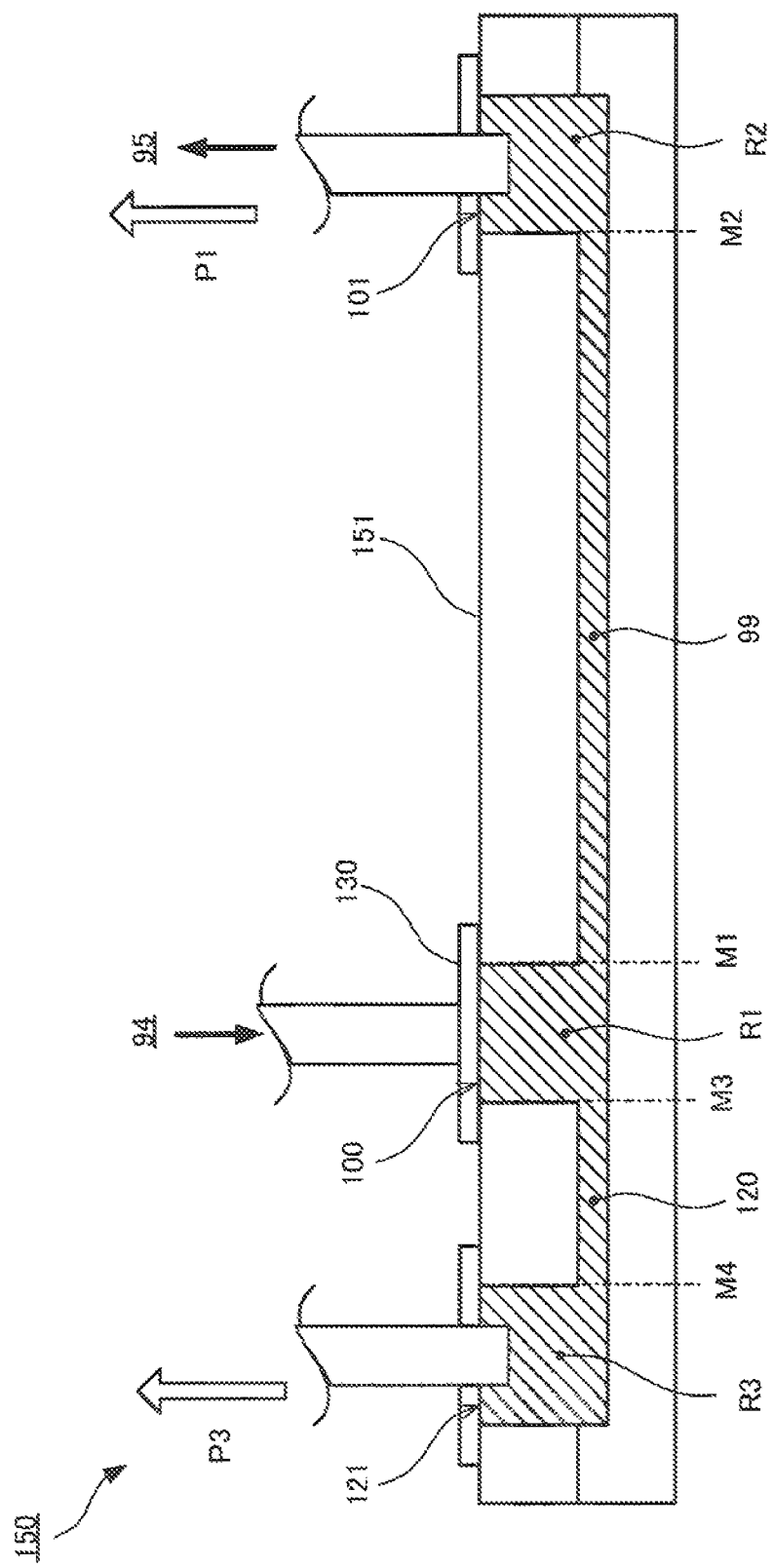
FIG. 17 is partial view that includes a microchip of the electrophoresis apparatus of the third embodiment.

FIG. 16 is a diagram illustrating the construction of an electrophoresis apparatus 150 of a third embodiment of the present invention. FIG. 17 is a partial view that includes the microchip 151 of an electrophoresis apparatus 150 of a third embodiment. The electrophoresis apparatus 150 of this third embodiment comprises an auxiliary flow channel for applying suction to the stored fluid L in the capillary flow channel 99. The other construction is the same as that of the electrophoresis apparatus 80 of the second embodiment illustrated in FIG. 9 and FIG. 11.

The microchip 151 comprises: an auxiliary channel 120 that connects to the capillary flow channel 99 via the reservoir R1 and an auxiliary hole 121 that is form on the other end section of the auxiliary channel 120 in addition to the construction of the microchip 85 illustrated in FIG. 9 and FIG. 11. The auxiliary hole 121 passes through the substrate 85a, and the spatial section that extends up to the auxiliary channel 120 is called reservoir R3.

The reservoir R3 is connected to the capillary flow channel 99 via the auxiliary channel 120, and is located in the end section of the auxiliary channel 120 that is far from the capillary flow channel 99. It is possible to suck solution such as stored fluid L that is in the capillary flow channel from the reservoir R3 via the auxiliary channel 120.

By applying suction with a suction force of P3 using a suction pump 131 that is provided in the end section of the auxiliary channel 120, pre-processing fluid flows to the reservoir R3 via the auxiliary channel 120. When doing this, the pre-processing fluid near the area of the reservoir R1 that is connected to the auxiliary channel 120 is sucked by the suction force P3.

The reservoir R3 differs from reservoirs R1 and R2 in that it does not need to be filled with solution. This is because during analysis, only the stored fluid L flows in the capillary flow channel 99, so the auxiliary channel 120 and the reservoir R3 are only used during cleaning.

In the reservoirs R1 and R2, it is difficult for solution to move in the low corner sections, and particularly, the low corner section that is paired with the capillary flow channel 99 side are sections where flow is difficult. In other words, the low corner sections are areas where it is easy for a previous analysis specimen to remain. Especially, it is easy for an analysis specimen to remain in the low corner section that is paired with the capillary flow channel 99 side of the reservoir R1, so by providing an auxiliary channel 120 in that location and generating flow of solution, it becomes possible to improve the cleaning efficiency of the reservoir R1.

Moreover, it is possible to apply suction to the reservoir R1 on the side having the auxiliary channel 120, which has the effect of making it easier to fill the reservoir R1 with solution.

It becomes easier to remove solution from the capillary flow channel 99, and there is no fear of mixing with the solution that will be used next, thus it is possible to further improve the cleaning efficiency.

Next, FIG. 12 and FIG. 16 to FIG. 18 will be used to explain the processing executed by the electrophoresis apparatus 150 of this third embodiment. The basic flow of this processing is the same as that of the processing explained in the second embodiment.

Figure 18:
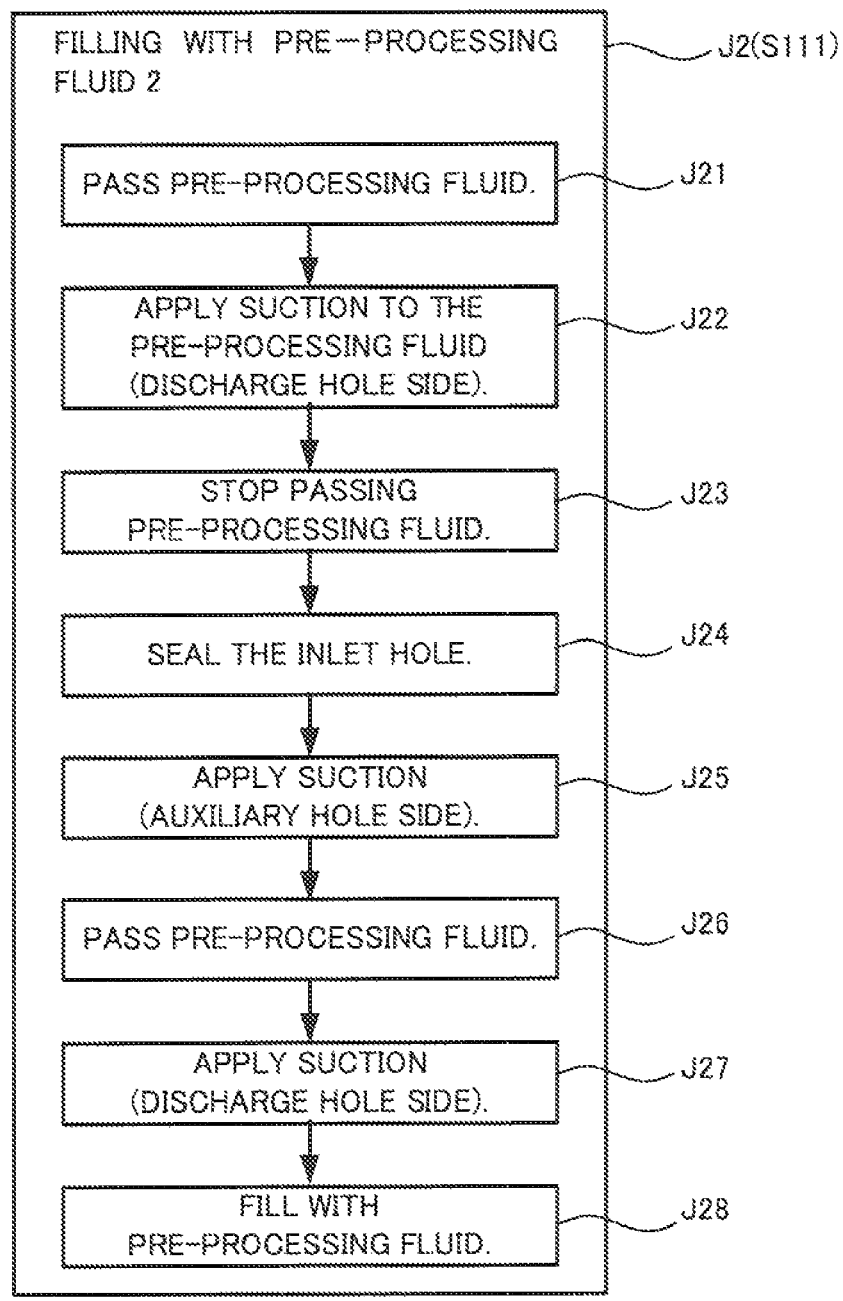
FIG. 18 is a flowchart illustrating part of the cleaning process of the pre-processing that is executed by the electrophoresis apparatus of the third embodiment.

FIG. 18 is a flowchart illustrating part of the cleaning process of the pre-processing process that is executed by the electrophoresis apparatus 150 of this third embodiment. In the following, filling with pre-processing fluid (step S111) is explained as filling 2 with pre-processing fluid (J2).

First, pre-processing fluid is caused to flow through the capillary flow channel 99 by introducing pre-processing fluid into the capillary flow channel 99 from the flow channel 94 via the inlet hole 100, and at the same time, the pre-processing fluid is discharged from the flow channel 112 via the discharge hole 101 (step J21).

Next, the suction pump 90 applies suction having a suction force P1 to the pre-processing fluid passing through the capillary flow channel 99 (step J22). As a result, pre-processing fluid in the capillary flow channel 99 vigorously flows toward the discharge hole 101, and the reservoir R2 can be filled with pre-processing fluid.

Once the flow of pre-processing fluid to the capillary flow channel 99 has stopped (step J23) and the reservoirs R1, R2 and the capillary flow channel 99 are filled with pre-processing fluid, the spatial section on the inlet hole 100 side, or in other words, the reservoir R1 is covered and sealed from the outside with a sealing member 130 (step J24). Then, the suction pump 131 applies suction having a suction force P3 to the capillary flow channel 99 via the auxiliary channel 120, and sucks the pre-processing fluid that is flowing in the capillary flow channel 99 (step J25).

After that, the sealing member 130 that covered and sealed the reservoir R1 is removed, and pre-processing fluid is again allowed to flow from the flow channel 94 into the capillary flow channel 99 via the inlet hole 100 (step J26).

The suction pump 90 then generates a suction force P1 and sucks the pre-processing fluid that flows in the capillary flow channel 99 (step J27). From this passing fluid, the capillary flow channel 99 is filled with pre-processing fluid, and the reservoirs R1, R2 are also filled with pre-processing fluid (step J28).

As was explained above, with the electrophoresis apparatus of this third embodiment, in the pre-processing process, and particularly in the cleaning process, it is possible to reduce the mechanical load on the flow channel of the microchip and to improve the cleaning efficiency.

It also becomes possible to adequately fill the capillary flow channel and reservoirs with solution, and to clean the minute areas and improve the cleaning efficiency, and as a result, the microchip can be used repeatedly during analysis and the number of times the microchip can be repeatedly used also increases. Moreover, by applying suction during cleaning, the burden on the microchip can be reduced, the fear of the joined surfaces of the substrates of the microchip coming apart is eliminated, and the durability of the microchip is improved.

Furthermore, by providing a flow channel (auxiliary channel) that is separate from the capillary flow channel, flow of solution is generated at and near the low corner sections of the reservoir, so it becomes possible to further improve the cleaning efficiency. The solution remaining in the capillary flow channel can be removed and mixing with the next solution to be used can be prevented, so the cleaning efficiency can be further improved.

In this third embodiment, an example of providing an auxiliary channel on the inlet hole side was explained; however it is also possible to provide the auxiliary channel on the discharge hole side, or on both sides. By removing the pre-processing fluid from the auxiliary channel side during cleaning, it is possible to prevent impurities from adhering again during cleaning.

The electrophoresis apparatus of the embodiments is not limited to the examples given above. The detailed design of the construction of the electrophoresis apparatus of the present invention can undergo various changes. For example, the design of the flow channel or the number of storage tanks, the positions of each of the features, the shapes of the features, and the like can be designed to correspond to the usage.

Moreover, in the embodiments above, for convenience of explanation, the number suction pumps used was one; however, a suction pump can be provided on both the inlet side and discharge side of the capillary flow channel of the microchip. Also, an auxiliary channel can be connected to the reservoirs on both ends of the capillary flow channel, and can be arbitrarily set.

The number of capillary channels is not limited to one and could be more than one. The construction of the capillary flow channel is not limited to a so-called straight form, and could, for example, be a cross-junction type in which two flow channels cross.

Analysis is performed using a capillary electrophoresis method, and for the data to be detected, data for a chromatogram can be analyzed as an electropherogram, and data for the dissolution time can be analyzed as the movement time, and the calculated parameter can be used as indices. The measurement object of the electropherogram is a reference specimen and proximate specimen, and cleaning and replacement of the microchip can be managed according to the parameters obtained by acquiring this electropherogram. Peak identification calculation such as fitting calculation can be used for the calculation, and the peak separation, retention time or half value width can be used as indices.

Furthermore, a cleaning unit provided in the electrophoresis apparatus for cleaning the capillary flow channel, as shown in Embodiments 1 to 3, is not limited to a unit that reserves the cleaning solution and fills the capillary flow channel with the cleaning solution according to the output of the cleaning signal. For example, a cleaning unit that is capable of filling the capillary flow channel with tap water may be provided in the electrophoresis apparatus. In this case, the cleaning unit fills the capillary flow channel with tap water according to the output of the cleaning signal to clean the capillary flow channel.

In addition, the following construction is included as preferred forms of the present invention.

The electrophoresis apparatus of a first aspect of the present invention is preferably characterized by comprising:
a physical quantity acquisition unit (71) that acquires an electrical quantity amount at the time that voltage applied to electrodes is started.

The electrophoresis apparatus is preferably characterized by further comprising:
a cleaning determination unit (74) that, when it is determined that the electrical quantity is not within a specified range by the physical quantity determination unit (72), outputs a cleaning signal in order to clean the capillary flow channel (47, 99).

The electrophoresis apparatus is preferably characterized by further comprising:
a replacement unit (75) that outputs a replacement signal for replacing a component of the capillary flow channel (47, 99); wherein the physical quantity acquisition unit (71) acquires the electrical quantity at every specified time when voltage is applied to the electrodes (21, 22, 86, 87);
the physical quantity determination unit (72) determines whether or not the electrical quantity is within the specified range every time the electrical quantity is acquired by the physical acquisition unit (71);
the cleaning determination unit (74) outputs the cleaning signal every times the physical quantity determination unit (72) determines that the electrical quantity is not within the specified range; and
the replacement unit (75) outputs the replacement signal without the cleaning signal being outputted, when the number of times that the physical quantity determination unit (72) continuously determined that the electrical quantity was not within the specified range has reached a first specified number of times.

The electrophoresis apparatus is preferably characterized by further comprising:
a memory unit (73) that stores the electrical quantity that the physical quantity acquisition unit (71) acquires; and
a temperature adjustment unit (76) that outputs a temperature adjustment signal in order to adjust the temperature of the components of the capillary flow channel (47, 99); wherein the physical quantity acquisition unit (71) acquires at specified time intervals an electrical quantity that occurs in the capillary flow channel (47, 99) while voltage is being applied to the electrodes (21, 22, 86, 87);
the physical quantity determination unit (72), every time the physical quantity acquisition unit (71) acquires the electrical quantity, calculates the difference between that electrical quantity and the electrical quantity that is stored in the past in the memory unit (73), and determines whether or not that difference exceeds a specified value; and
the temperature adjustment unit (76) outputs a temperature adjustment signal when the physical quantity determination unit (72) determines that the difference exceeds the specified value.

The electrophoresis apparatus is preferably characterized by further comprising:
a replacement unit (75) that outputs a replacement signal for replacing a component of the capillary flow channel (47, 99); wherein
the temperature adjustment unit (76) outputs a temperature adjustment signal every time the physical quantity determination unit (72) determines that the difference between the electrical quantities exceeds a specified value; and
the replacement unit (75) outputs the replacement signal without a temperature adjustment signal being outputted when the number of times that the physical quantity determination unit (72) determined that the difference between the electrical quantities exceeded the specified value reaches a second specified number of times.

The electrophoresis apparatus is preferably characterized by further comprising:
a memory unit (73) that stores the electrical quantity that the physical quantity acquisition unit (71) acquires; and
a voltage change unit (77) that changes the size of the voltage that is applied to the electrodes (21, 22, 86, 87); wherein
the physical quantity acquisition unit (71) acquires at specified time intervals an electrical quantity that occurs in the capillary flow channel (47, 99) while voltage is being applied to the electrodes;
the physical quantity determination unit (72), every time the physical quantity acquisition unit (71) acquires the electrical quantity, calculates the difference between that electrical quantity and the electrical quantity that is stored in the past in the memory unit (73), and determines whether or not that difference exceeds a specified value; and
the voltage change unit (77) calculates a correction value for the voltage applied to the electrodes (21, 22, 86, 87) and changes the size of the voltage applied to the electrodes (21, 22, 86, 87) to the correction value when the physical quantity determination unit (72) determines that the difference exceeds the specified value.

The voltage change unit (77) is preferably characterized by calculating the correction value based on the electrical quantity whose difference with the electrical quantity that is stored in the past does not exceed the specified value.

The voltage change unit (77) is preferably characterized by calculating the correction value based on a preset target value for the electrical quantity.

The electrophoresis apparatus is preferably characterized by further comprising:
a replacement unit (75) that outputs a replacement signal for replacing a component of the capillary flow channel (47, 99); wherein
the voltage change unit (77) changes the voltage applied to the electrodes (21, 22, 86, 87) every time the physical quantity determination unit (72) determines that the difference between electrical quantities exceeds a specified value; and the replacement unit (75) outputs the replacement signal without the voltage applied to the electrodes (21, 22, 86, 87) being changed when the number of times that the physical quantity determination unit (72) has determined that the difference in electrical quantities has exceeded the specified value has reached a second specified number of times.

The electrophoresis apparatus is preferably characterized by further comprising:

a voltage value calculation unit (78) that calculates the value of the voltage to be applied to the electrodes the next time based on the electrical quantity stored in the memory unit (73); wherein the electrophoresis apparatus (1, 80, 140, 150) applies the voltage calculated by the voltage calculation unit (78) to the electrodes (21, 22, 86, 87).

The electrophoresis apparatus is preferably characterized in that the electrical quantity is the electric current that flows between the electrodes (21, 22, 86, 87) according to the voltage that is applied to the electrodes (21, 22, 86, 87).

The electrophoresis apparatus is characterized by preferably further comprising:

a microchip (85, 141, 151) that has the capillary flow channel (99), and reservoirs (R1, R2) that connect to the ends of the capillary flow channel (99) and that can store solution;

a dispensing unit (84) that dispenses solution to the capillary flow channel (99); and a suction unit that applies suction to the solution inside the reservoirs (R1, R2) and inside the capillary flow channel (99) from outside of the reservoirs (R1, R2).

The electrophoresis apparatus is preferably characterized in that the dispensing unit (84) also functions as the suction unit that applies suction to the solution inside the reservoirs (R1, R2) and inside the capillary flow channel (99).

The electrophoresis apparatus is preferably characterized by comprising:

an auxiliary channel (120) that connects to the capillary flow channel (99) via the reservoir (R1), and is a different channel than the capillary flow channel (99);

a sealing unit (130) that seals the reservoir (R1), which connects to the auxiliary channel (120), from outside; and a second suction unit (131) that applies suction to the solution inside the reservoir (R1) and inside the capillary flow channel (99) from the other end section of the auxiliary channel (120).

The control method for an electrophoresis apparatus of a second aspect of the present invention is preferably characterized in that:

a microchip (85, 141, 151) having the capillary flow channel (99), and reservoirs (R1, R2) that are connected to the ends of the capillary flow channel (99) and that are capable of storing solution are provided in the electrophoresis apparatus (80, 140, 150), and the control method comprises:

a cleaning process that includes at least one time each of a filling process that fills the reservoirs (R1, R2) and the capillary flow channel (99) with pre-processing fluid, and a discharge process that applies suction from the outside of the reservoir (R1) on one of the ends of the capillary flow channel (99) to the pre-processing fluid that was filled in the reservoirs (R1, R2) and capillary flow channel (99) and removes the pre-processing fluid from the reservoirs (R1, R2) and capillary flow channel (99);

a dispensing process of filling buffer solution into the capillary flow channel (99) and dispensing the specimen that is the object of measurement into the capillary flow channel (99);

a process of applying voltage to both ends of the capillary flow channel (99) and performing electrophoresis; and a process of detecting the measurement results of electrophoresis.

The control method for the electrophoresis apparatus is preferably characterized in that in the discharge process the dispensing unit (84), which is used when dispensing the specimen in the dispensing process, applies suction to the pre-processing fluid from the outside of the reservoir (R1) on the side where the specimen is dispensed.

The control method for the electrophoresis apparatus is preferably characterized in that the discharge process seals the reservoir (R1) from the outside, and applies suction to the pre-processing fluid inside the capillary flow channel (99) from the outside on the far end from the capillary flow channel (99) of an auxiliary channel (120) that is a flow channel that is different from the capillary flow channel (99) and that connects to the capillary flow channel (99) via the reservoir (R1).

Having described and illustrated the principles of this application by reference to one or more preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. An electrophoresis apparatus that applies voltage from electrodes that are provided in a capillary flow channel and causes component separation by performing electrophoresis on a specimen that is injected into the capillary flow channel, the electrophoresis apparatus comprising a controller including:

a physical quantity acquisition unit that, with a migration solution and a specimen injected inside the capillary flow channel, is configured to acquire an electrical quantity that occurs in the capillary flow channel at a specified time when voltage is being applied to the electrodes;

a physical quantity determination unit that is configured to determine whether or not the electrical quantity is within a specified range;

a cleaning determination unit that, when the physical quantity determination unit determines that the electrical quantity is not within the specified range, is configured to output a cleaning signal for cleaning the capillary flow channel; and a replacement unit that is configured to output a replacement signal for replacing a component of the capillary flow channel;

wherein the controller is programmed to control:

the physical quantity acquisition unit to acquire the electrical quantity at every specified time when voltage is being applied to the electrodes;

the physical quantity determination unit to determine whether or not the electrical quantity is within the specified range every time that the physical quantity acquisition unit acquires the electrical quantity;

the cleaning determination unit to output the cleaning signal every time the physical quantity determination unit determines that the electric quantity is not within the specified range; and the replacement unit to output the replacement signal without the cleaning signal being outputted when the number of times that the physical quantity determination unit continuously determines that the electrical quantity is not within the specified range reaches a first specified number of times.

2. The controller of the electrophoresis apparatus according to claim 1, wherein
the physical quantity acquisition unit is configured to acquire the electrical quantity at the start of the application of voltage to the electrodes.

3. The controller of the electrophoresis apparatus according to claim 1, further comprising:
a memory unit that is configured to store the electrical quantity that the physical quantity acquisition unit acquires; and
a temperature adjustment unit that is configured to output a temperature adjustment signal for adjusting the temperature of a component of the capillary flow channel;
wherein the controller is ed to control:
the physical quantity acquisition unit to acquire an electrical quantity that occurs in the capillary flow channel at specified time intervals while voltage is being applied to the electrodes;
the physical quantity determination unit, every time the physical quantity acquisition unit acquires the electrical quantity, to calculate the difference between that electrical quantity and the electrical quantity that was stored in the memory unit in the past, and to determine whether or not that difference exceeds a specified value; and
the temperature adjustment unit to output the temperature adjustment signal when the physical quantity determination unit determines that the difference exceeds the specified value.

4. The controller of the electrophoresis apparatus according to claim 3, further comprising:
a replacement unit that is configured to output a replacement signal for replacing a component of the capillary flow channel;
wherein the controller is programmed to control:
the temperature adjustment unit to output the temperature adjustment signal every time the physical quantity determination unit determines that the difference between the electrical quantities exceeds a specified value; and
the replacement unit to output the replacement signal without a temperature adjustment signal being outputted when the number of times that the physical quantity determination unit determined that the difference between the electrical quantities exceeded a specified value reaches a second specified number of times.

5. The controller of the electrophoresis apparatus according to claim 1, further comprising:
a memory unit that is configured to store the electrical quantity that the physical quantity acquisition unit acquires; and
a voltage change unit that is configured to change the size of the voltage that is applied to the electrodes;
wherein the controller is programmed to control:
the physical quantity acquisition unit to acquire an electrical quantity that occurs in the capillary flow channel at specified time intervals while voltage is being applied to the electrodes;
the physical quantity determination unit, every time that the physical quantity acquisition unit acquires the electrical quantity, to calculate the difference between the electrical quantity and the electrical quantity that was stored in the memory unit in the past, and to determine whether or not that difference exceeds a specified value; and
the voltage change unit, when the physical quantity determination unit determines that the difference exceeds the specified value, to calculate a correction value for the voltage applied to the electrodes, and to change the size of the voltage applied to the electrodes to the correction value.

6. The controller of the electrophoresis apparatus according to claim 5, wherein
the voltage change unit is configured to calculate the correction value based on an electrical quantity whose difference with the electrical quantity that was stored in the past does not exceed the specified value.

7. The controller of the electrophoresis apparatus according to claim 5, wherein
the voltage change unit is configured to calculate the correction value based on a preset target value for the electrical quantity.

8. The controller of the electrophoresis apparatus according to claim 5, further comprising:
a replacement unit that is configured to output a replacement signal for replacing a component of the capillary flow channel;
wherein the controller is programmed to control:
the voltage change unit to change the voltage applied to the electrodes every time the physical quantity determination unit determines that the difference between the electrical quantities exceeds a specified value; and
the replacement unit to output the replacement signal without the voltage applied to the electrodes being changed, when the number of times that the physical quantity determination unit determined that the difference between the electrical quantities exceeded a specified value reaches a second specified number of times.

9. The controller of the electrophoresis apparatus according to claim 3, further comprising:
a voltage value calculation unit that, based on the electrical quantity stored in the memory unit, is configured to calculate the value of the voltage to be applied to the electrodes the next time.

10. The electrophoresis apparatus according to claim 1, wherein
the electrical quantity is the electrical current that flows between the electrodes when voltage is applied to the electrodes.

11. The electrophoresis apparatus according to claim 1, comprising:
a microchip having the capillary flow channel, and reservoirs that are connected to the ends of the capillary flow channel and that are capable of storing solution;
a dispensing unit that is configured to dispense solution to the capillary flow channel; and
a suction unit that is configured to apply suction to the solution inside the reservoirs and inside the capillary flow channel from the outside of the reservoirs.

12. The electrophoresis apparatus according to claim 11, wherein
the dispensing unit also functions as the suction unit that is configured to apply suction to the solution inside the reservoirs and inside the capillary flow channel.

13. The electrophoresis apparatus according to claim 11, further comprising:
an auxiliary channel, which is a channel that is connected to the capillary flow channel via a reservoir and that is different than the capillary flow channel;
a sealing unit that is configured to seal the reservoir that connects to auxiliary channel from outside; and a second suction unit that is configured to apply suction to the solution inside the reservoirs and inside the capillary flow channel from the other end section of the auxiliary channel.

14. A control method for an electrophoresis apparatus that applies voltage from electrodes that are provided in a capillary flow channel in order to separate components of a specimen injected inside the capillary flow channel by electrophoresis, the control method comprising:

a physical quantity acquisition step that, with migration solution and specimen injected inside the capillary flow channel, acquires an electrical quantity that occurs in the capillary flow channel at a specified time when voltage is being applied to the electrodes;

a physical quantity determination step of determining whether or not the electrical quantity is within a specified range;

a cleaning determination step of outputting a cleaning signal for cleaning the capillary flow channel, when the physical quantity determination step determines the electrical quantity is not within the specified range; and a replacement step of outputting a replacement signal for replacing a component of the capillary flow channel;

wherein the physical quantity acquisition step acquires the electrical quantity at every specified time when voltage is being applied to the electrodes;

the physical quantity determination step determines whether or not the electrical quantity is within the specified range every time that the physical quantity acquisition unit acquires the electrical quantity;

the cleaning determination step outputs the cleaning signal every time the physical quantity determination unit determines that the electric quantity is not within the specified range; and the replacement step outputs the replacement signal without the cleaning signal being outputted when the number of times that the physical quantity determination step continuously determines that the electrical quantity is not within the specified range reaches a first specified number of times.

15. The control method for an electrophoresis apparatus according to claim 14, wherein a microchip having the capillary flow channel and reservoirs that are connected to the ends of the capillary flow channel and are capable of storing solution is provided in the electrophoresis apparatus, the control method comprising:

a cleaning process that includes at least one time each of a filling process that fills the reservoirs and the capillary flow channel with pre-processing fluid, and a discharge process that applies suction from the outside of the reservoir on one of the ends of the capillary flow channel to the pre-processing fluid that was filled in the reservoirs and capillary flow channel and removes the pre-processing fluid from the reservoirs and capillary flow channel;

a dispensing process that fills buffer solution into the capillary flow channel and dispenses the specimen that is the object of measurement into the capillary flow channel;

a process of applying voltage to both ends of the capillary flow channel and performing electrophoresis; and a process of detecting the measurement results of electrophoresis.

16. The control method for an electrophoresis apparatus according to claim 15, wherein the discharge process, with a dispensing unit which is used when dispensing the specimen in the dispensing process, applies suction to the pre-processing fluid from the outside of the reservoir on the side where the specimen is dispensed.

17. The control method for the electrophoresis apparatus according to claim 15, wherein the discharge process seals the reservoir from the outside, connects to the capillary flow channel via the reservoir, and applies suction to the pre-processing fluid inside the capillary flow channel from the outside on the far end from the capillary flow channel of an auxiliary channel that is a flow channel that is different from the capillary flow channel.

* * * * *